(12) United States Patent
LeCloux et al.

(10) Patent No.: US 8,071,975 B2
(45) Date of Patent: Dec. 6, 2011

(54) ELECTRONIC DEVICES MADE WITH ELECTRON TRANSPORT AND/OR ANTI-QUENCHING LAYERS

(75) Inventors: Daniel D. LeCloux, Wilmington, DE (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 626 days.

(21) Appl. No.: 11/835,047

(22) Filed: Aug. 7, 2007

(65) Prior Publication Data

US 2009/0121617 A1 May 14, 2009

Related U.S. Application Data

(62) Division of application No. 10/612,482, filed on Jul. 2, 2003, now Pat. No. 7,265,378.

(60) Provisional application No. 60/394,767, filed on Jul. 10, 2002, provisional application No. 60/458,277, filed on Mar. 28, 2003, now abandoned.

(51) Int. Cl.
*H01L 51/00* (2006.01)
*H01L 51/54* (2006.01)

(52) U.S. Cl. .................... 257/40; 257/431; 257/E51.05; 313/506; 428/917; 136/263

(58) Field of Classification Search ........................ None
See application file for complete search history.

(56) References Cited

U.S. PATENT DOCUMENTS

| | | |
|---|---|---|
| 3,423,427 A | 1/1969 | Cescon et al. |
| 3,449,379 A | 6/1969 | Cescon et al. |
| 3,666,466 A | 5/1972 | Strilko |
| 3,739,000 A | 6/1973 | Lodolini et al. |
| 4,140,529 A | 2/1979 | Pai et al. |
| 4,304,829 A | 12/1981 | Limburg et al. |
| 4,579,679 A | 4/1986 | Papir |
| 4,853,090 A | 8/1989 | Daniel et al. |
| 4,996,124 A | 2/1991 | Buettner et al. |
| 5,077,142 A | 12/1991 | Sakon et al. |
| 5,294,810 A * | 3/1994 | Egusa et al. .................... 257/40 |
| 5,545,639 A | 8/1996 | Rabinovitz et al. |
| 6,004,709 A | 12/1999 | Renfer et al. |
| 6,232,714 B1 | 5/2001 | Shen et al. |
| 6,307,528 B1 | 10/2001 | Yap |
| 6,310,360 B1 | 10/2001 | Forrest et al. |
| 6,344,505 B1 | 2/2002 | Valentine, Jr. et al. |
| 6,716,371 B1 | 4/2004 | Sage et al. |
| 6,723,445 B2 | 4/2004 | Li et al. |
| 6,740,407 B1 | 5/2004 | Usuki et al. |
| 7,265,378 B2 * | 9/2007 | Lecloux et al. .................. 257/40 |

(Continued)

FOREIGN PATENT DOCUMENTS

EP 0341859 A1 11/1989

(Continued)

OTHER PUBLICATIONS

Machine translation for JP 7-26255 A (Jan. 1995).*

(Continued)

*Primary Examiner* — Marie R. Yamnitzky

(57) ABSTRACT

The present invention is directed to a photoactive device comprising an anode, a cathode, and a photoactive layer, which device further comprises an electron transport and/or anti-quenching layer which minimizes both electron transfer quenching and energy transfer quenching of the photoactive layer.

3 Claims, 25 Drawing Sheets

U.S. PATENT DOCUMENTS

| | | | |
|---|---|---|---|
| 2002/0045061 | A1 | 4/2002 | Hosokawa |
| 2002/0055015 | A1 | 5/2002 | Sato et al. |
| 2002/0135292 | A1 | 9/2002 | Kamatani et al. |
| 2003/0197158 | A1 | 10/2003 | Lee et al. |
| 2004/0077860 | A1 | 4/2004 | Herron et al. |

FOREIGN PATENT DOCUMENTS

| | | | |
|---|---|---|---|
| EP | 0564224 | A2 | 10/1993 |
| EP | 1013740 | A2 | 6/2000 |
| EP | 1 097 981 | A2 | 5/2001 |
| EP | 1182183 | A1 | 2/2002 |
| EP | 1 215 945 | A2 | 6/2002 |
| FR | 2099783 | A5 | 3/1972 |
| GB | 1047796 | | 11/1966 |
| JP | 55-017105 | A | 2/1980 |
| JP | 55-098754 | A | 7/1980 |
| JP | 60-106858 | A | 6/1985 |
| JP | 61-051151 | A | 3/1986 |
| JP | 62-174981 | A | 7/1987 |
| JP | 01-103484 | A | 4/1989 |
| JP | 01-208873 | A | 8/1989 |
| JP | 05-247357 | A | 9/1993 |
| JP | 6-86072 | | 3/1994 |
| JP | 7-26255 | A * | 1/1995 |
| WO | WO 99/48160 | A1 | 9/1999 |
| WO | WO 00/70655 | A2 | 11/2000 |
| WO | 0172925 | A1 | 10/2001 |
| WO | 0230159 | A1 | 4/2002 |
| WO | 0243449 | A1 | 5/2002 |
| WO | WO 02/51206 | A2 | 6/2002 |
| WO | 02088274 | A1 | 11/2002 |
| WO | WO 02/091814 | A2 | 11/2002 |
| WO | WO 02/101838 | A1 | 12/2002 |
| WO | 03079737 | A2 | 9/2003 |

OTHER PUBLICATIONS

H. Schurmann et al., "Ultraviolet Photoelectron Spectroscopic Study of Heterocyclic Model Compounds for Electroluminescent Devices", Synthetic Metals 102 (1999), pp. 1069-1070.*
Zhu, Lihua et al., A relationship between driving voltage and the highest occupied molecular orbital level of hole-transporting metallophthalocyanine layer for organic electroluminescence devices, Thin Solid Films, 2001, 213-218, 396, Elsevier Science B.V.
Naka, Shigeki et al., High electron mobility in bathophenanthroline, Applied Physics Letters, Jan. 10, 2000, 197-199, 76(2), American Institute of Physics.
Dietrich-Buchecker, Christiane et al., Selective and efficient synthesis di-, tri- and tetrasubstituted 1,10-phenanthrolines, Tetrahedron Letters, 1999, 3395-3396, 40, Elsevier Science Ltd.
Thomas, K.R. Justin et al., Quinoxalines Incorporating Triarylamines: Potential Electroluminescent Materials with Tunable Emission Characteristics, Chem. Mater., 2002, 2796-2802, 14, American Chemical Society.
Yamamoto, Takakazu et al., Preparation of New Electron-Accepting-Conjugated Polyquinoxalines. Chemical and Electrochemical Reduction, Electrically Conducting Properties, and Use in Light-Emitting Diodes. J. Am. Chem. Soc., 1996, 3930-3937, 118, American Chemical Society.
Redecker, M. et al., Electron transport in starburst phenylquinoxallnes. Applied Physics Letter, Jul. 5, 1999, 109-111, 75(1), American Institute of Physics.
Adachi et al., Nearly 100% Internal Phosphorescence Efficiency In An Organic light Emitting Device, Journal Of Applied Physics, Nov. 15, 2001, vol. 90, pp. 5048-5051.
Beilstein Record No. 8797439(2006).
Borsenberger, P.M. et al., Hole Transport in Vapor-Deposited Triphenylmethane Glasses, Jpn. J. Appl. Phys., May 1996, 2698-2703, vol. 35, Pt. 1, No. 5A.
Borsenberger, Paul M. et al., Effects of the Dipole Moment on Charge Transport in Disordered Molecular Solids, The Journal of Physical Chemistry, 1993, 4815-4819, 97(18), American Chemical Society.
Chao et al, Effect of Side Chain Alkyl Length on the Electroluminescence Characteristics fo Carbazole-Based Light Emitting Polymers, Macromol, Chem Phys. 200 pp. 2864-2871, 202 (14).
Cui, Yuanting et al., Thiophene-Linked Polyphenylquinoxaline: A New Electron Transport Conjugated Polymer for Electroluminescent Devices, Macromolecules, 1999, 3824-3826, 32, American Chemical Society.
Gibson, Harry W. et al., Surface Analyses by a Triboelectric Charging Technique, Analytical Chemistry, Apr. 1979, 483-487, 51(4) American Chemical Society.
Giebeler, C. et al., The photovoltaic effect in poly(p-phenylene-2,3'-bis(3,2'-diphenyl)-quinoxaline-7-7'-diyl), Optical Materials, Jan. 1998, 99-103, 9, Elsevier Science B.V.
Gruenbaum, W. T. et al., Hole Transport in Triphenylmethane Doped Polymers, Jpn. J. Appl. Phys., May 1996, 2704-2708, vol. 35, Pt. 1, No. 5A.
Jandke, Markus et al., Phenylquinoxaline Polymers and Low Molar Mass Glasses as Electron-Transport Materials in Organic Light-Emitting Diodes, Macromolecules, 1998, 6434-6443, 31, American Chemical Society.
Jin, Sung-Ho et al., Blue electroluminescence in blend of polymers containing carbazole and 1,3,4-oxadiazole units, Thin Solid Films, 2000, 255-258, 363, Elsevier Science S.A.
Kuder, James E. et al., Anodic and Photochemical Oxidation of Triphenylmethanes, J. Org. Chem., 1979, 761-766, vol. 44, American Chemical Society.
Limburg, W. et al., Electronic Transport Properties of Molecularly Doped Polymers—Some Substituted Triarylmethanes, Organic Coatings and Plastics, Chemistry, 1978, 534-539, 38.
Malpert, John H. et al., Color intensity control in polymers using triarylmethane leuconitriles as color formers, Tetrahedron, 2001, 967-974, 57, Elsevier Science Ltd.
Nguyen, T. P. et al., Multilayer light emitting diodes using a PPV based copolymer, Optical Materials, Jan. 1998, 154-158, 9, Elsevier Science B.V.
O'Brien, D. et al., Use of poly(phenyl quinoxaline) as an electron transport material in polymer light-emitting diodes, Appl. Phys. Lett., Aug. 12, 1996, 881-883, 69(7), American Institute of Physics.
Patent Abstracts of Japan, Electrophotographic Sensitive Body, JP02064553, Mar. 5, 1990, vol. 14, No. 245, Canon Inc.
Patent Abstracts of Japan, Organic Thin-Film El Element, JP04110390, Apr. 10, 1992, vol. 16, No. 358, Nippon Soda Co. Ltd.
Patent Abstracts of Japan, Organic Electroluminescent Element, JP06088072, Mar. 29, 1994, vol. 18, No. 347,Idemitsu Kosan Co. Ltd.
Patent Abstracts of Japan, Organic El Element, JP07026255, Jan. 27, 1995, vol. 1994, No. 4, Idemitsu Kosan Co Ltd.
Patent Abstracts of Japan, Electrophotographic Photoreceptor, JP07152170, Jun. 16, 1995, vol. 1995, No. 9, Mita Ind Co Ltd.
Patent Abstracts of Japan, Organic El Element Using Quinoxaline Compound, JP09188874, Jul. 22, 1997, vol. 1997, No. 11, TDK Corp.
Patent Abstracts of Japan, Electrophotographic Sensitive Body, JP61041152, Feb. 27, 1986, vol. 10, No. 198.
Patent Abstracts of Japan, Organic Electroluminescent Element and Its Manufacture, JP2000133453, May 12, 2000, vol. 2000, No. 8, Idemitsu Kosan Co Ltd.
Patent Abstracts of Japan, Organic Thin Film EL Element and Quinoxalino-Benzooxazine Derivative Used In The Element, JP2000198788, Jul. 18, 2000, vol. 2000, No. 10, Sagami Chem Res Center.
Patent Abstracts of Japan, Aromatic Methylidene Compound, Aromatic Aldehyde Compound For Producing The Same And Production Thereof, JP2000204082. Jul. 25, 2000, vol. 2000, No. 10, Matsushita Electric Ind. Co. Ltd.
Patent Abstracts of Japan, Novel Heterocyclic Compound, Light-Emitting, Element Material and Light-Emitting Element Using This Material, JP2001335776, Dec. 4, 2001, Fuji Photo Film Co Ltd.
Patent Abstracts of Japan, Organic Electroluminescent Element And Display Device, JP2003045662, Feb. 14, 2003, vol. 2003, No. 6, Konica Corp.
Patent Abstracts of Japan, Light-Emitting Element, JP2003086381, Mar. 20, 2003 vol. 2003, No. 7, Toray Ind Inc.
JP2001110572, Field Light Emitting Element, Patent Abstracts of Japan, Apr. 20, 2001, vol. 2000, No. 26, Toray Ind. Inc.

JP2001267080, Light Emission Element, Patent Abstracts of Japan, Sep. 28, 2001, vol. 2000, No. 26, Toray Ind. Inc.

JP2002352961, Organic Electroluminescent Device, Patent Abstracts of Japan, Dec. 6, 2002, vol. 2003, No. 4 Toray Ind. Inc.

Posch, P. et al., Perylenediimides with Electron Transport Moieties for Electroluminescent Devices, Synthetic Metals, 1999, 1110-1112, 102, Elsevier Science S.A.

Velten et al., Synthesis, solution properties and conversion of poly(2,9-o-phenanthroline-alt-(2',5'-dihexyl)-4,4"-p-terphenylene)s into soluble, well-defined copper(I) and silver (I) complex polymers, Macromol. Chem. Phys., 1998, 127-140, 199, Huthig & Wepf Verlag, Zug.

Schmitz, Christoph, et al., Polymeric Light-Emitting Diodes Based on Poly(p-phenylene ethynylene), Poly (triphenyldiamine), and Spiroquinoxaline, Advanced Functional Materials, 2001, 41-46, 11(1), Wiley-Vch Verlag GmbH.

Sun, Li-Xian et al., PVC membrane lithium-selective electrodes based on oligomethylene-bridged bis-1, 10-phenanthroline derivatives, Analytics Chimica Acta, 1996, 57-64, 329, Elsevier Science B.V.

Saitoh et al., Preparation and Properties of pi-Conjugated Poly(1,10-phenanthroline-3, 8-diyl), Chemistry Letters, 1995, 785-786.

Young, Ralph H. et al., Dipole Moments of Hole-Transporting Materials and Their Influence on Hole Mobility in Molecularly Doped Polymers, J. Phys. Chem., 1995, 4230-4240, 99(12), American Chemical Society.

Zhao et al., Photorefractive Polymer with Side-Chain Second Order Nonlinear Optical and Charge-Transporting Groups. Chem Mater 1995 (7) pp. 1237-1242.

Zotti, Gianni et al., Electrochemical, Conductive, and Magnetic Properties of 2,7-Carbazole-Based Conjugated Polymers, Macromolecules, 2002, 2122-2128, 35, American Chemical Society.

Borsenberger, P.M. et al., Hole Transport in Triphenylmethane-doped Poly(styrene), Journal of Imaging Science and Technology, vol. 41, No. 2, pp. 185-191, 1997.

Filler, R. et al, Flourocarbon Chemistry-Tris(4-nitro-2,3,5,6-tetra flourophenyl)methane and companions, Journal of Flourine Chemistry, vol. 102, pp. 185-188, Elsevier Science, 2000.

Hallas, G. et al, Dyes Containing Flourine-I; Electronic Absorbtion Spectrum of 2,3,4,5,6-Pentaflouro Malachite Green and the Effect of the Pentaflourophenyl Group, Tetrahedron, vol. 28, pp. 893-896, 1972.

Miyaura et al., A New Stereospecific Cross-Coupling by the Palladium-Catalyzed Reaction of 1-Alkenylboranes with 1-Alkenyl or 1-Alkynyl Halides, Tetrahedron Letters, No. 36, pp. 3437-3440, 1979.

Yamamoto et al, Electrically conducting and thermally stable pi-conjugated poly(arylene)s prepared by organometallic process, Progress in Polymer Science, vol. 17, pp. 1153-1205, 1992.

PCT International Search Report for International Application No. PCT/US 03/021613, D. Marsitzky Authorized Officer, Feb. 26, 2004.

PCT International Search Report for International Application No. PCT/US 03/021612, N. Doslik Authorized Officer, Mar. 15, 2004.

PCT International Search Report for International Application No. PCT/US 03/021610, M. Fritz Authorized Officer, Apr. 6, 2004.

PCT International Search Report for International Application No. PCT/US 03/021618, S. Fanni Authorized Officer, Jan. 28, 2004.

PCT International Search Report for International Application No. PCT/US 03/021617, C. Pusch Authorized Officer, Feb. 24, 2004.

* cited by examiner

I(a)

I(b)

I(c)

I(d)

I(e)

(II)

II(a)

II(b)

II(c)

II(d)

II(e)

II(f)

II(g)

II(h)

II(i)

III(a)

III(b)

IV(a)

IV(b)

IV(c)

IV(d)

IV(e)

IV(f)

IV(g)

IV(h)

(V)

V(a)

V(b)

V(c)

V(d)

V(e)

V(f)

g h i j

V(k)

V(l)

V(m)

V(n)

V(o)

V(p)

V(q)

V(r)

V(s)

V(t)

V(u)

V(v)

V(w)

V(x)

V(y)

V(z)

V(aa)

V(ab)

V(ac)

V(ad)

V(ae)

V(af)

V(ag)

(VI)

VI(a)

VI(b)

VI(c)

VI(d)

VI(j)

VI(k)

VII

DDPA (Compound A)

DPA (Compound B)

ELECTRONIC DEVICES MADE WITH ELECTRON TRANSPORT AND/OR ANTI-QUENCHING LAYERS

CROSS REFERENCE TO RELATED APPLICATIONS

This application is a divisional of U.S. application Ser. No. 10/612,482 filed Jul. 2, 2003, now U.S. Pat. No. 7,265,378, which claims priority from U.S. Provisional Application Ser. No. 60/394,767, filed Jul. 10, 2002, and U.S. Provisional Application Ser. No. 60/458,277, filed Mar. 28, 2003 now abandoned.

BACKGROUND OF THE INVENTION

1. Field of the Invention

The present invention relates to photoactive electronic devices in which there is at least one active layer comprising an electron transport and/or anti-quenching composition.

2. Description of the Related Art

In organic photoactive electronic devices, such as light-emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices which use photoactive materials, frequently include one or more charge transport layers, which are positioned between the photoactive (e.g., light-emitting) layer and one of the contact layers. A hole transport layer may be positioned between the photoactive layer and the hole-injecting contact layer, also called the anode. An electron transport layer may be positioned between the photoactive layer and the electron-injecting contact layer, also called the cathode.

When organometallic compounds, such as Ir and Pt complexes, are used as the electroluminescent layer, a blocking layer inserted next to the luminescent layer on the cathode side can enhance the device efficiency. 2,9-Dimethyl-4,7-diphenyl-1,10-phenanthroline (known as BCP or DDPA) was used by Baldo et al. for this purpose. It was proposed that the BCP layer functions as an "exciton blocker" to prevent the transfer of the energy of a luminescent exciton to the adjacent layer. The blocking layer is characterized by a band gap greater than the energy level of excitons formed in the luminescent layer.

U.S. Pat. No. 6,097,147 claims a light emitting device comprising: a substantially transparent anode; a hole transporting layer over said anode; an emission layer over said hole transporting layer; a blocking layer over said emission layer; an electron transporting layer over said blocking layer; and a cathode in electrical contact with said electron transporting layer. It further claims a device wherein said blocking layer is characterized by a band gap greater than the energy level of excitons formed in said emission layer.

However, energy transfer from photoactive materials to an adjacent layer can be quenched not only by energy transfer but also by electron transfer to the adjacent layer, so the use of larger band gap exciton blocker is insufficient. Materials that can prevent both energy transfer quenching and electron transfer quenching are needed.

SUMMARY OF THE INVENTION

The present invention is directed to a photoactive device comprising an anode, a cathode, and a photoactive layer, which device further comprises an electron transport and/or anti-quenching layer which minimizes both electron transfer quenching and energy transfer quenching of the photoactive layer.

In one embodiment is a photoactive electronic device comprising:
   (a) an anode;
   (b) a cathode, said cathode having a work function energy level $E_3$;
   (c) a photoactive layer positioned between said anode and said cathode, said photoactive layer comprising a cyclometallated complex of a transition metal, said cyclometalated complex having a LUMO energy level $E_2$ and a HOMO energy level $E_4$; and
   (d) an electron transport and/or anti-quenching layer positioned between said cathode and said photoactive layer, said electron transport and/or anti-quenching layer having a LUMO energy level $E_1$ and a HOMO energy level $E_5$,
with the proviso that:
   (1) $E_1 - E_3 < 1$ eV,
   (2) $E_1 - E_2 > -1$ eV, and
   (3) $E_4 - E_5 > -1$ eV.

As used herein, the term "charge transport composition" is intended to mean material that can receive a charge from an electrode and facilitates movement through the thickness of the material with relatively high efficiency and small loss of charge. Hole transport compositions are capable of receiving a positive charge from an anode and transporting it. Electron transport compositions are capable of receiving a negative charge from a cathode and transporting it. The term "anti-quenching composition" is intended to mean a material which prevents, retards, or diminishes both the transfer of energy and the transfer of an electron to/or from the excited state of the photoactive layer to an adjacent layer. The term "photoactive" refers to any material that exhibits electroluminescence, photoluminescence, and/or photosensitivity. The term "HOMO" refers to the highest occupied molecular orbital of a compound. The term "LUMO" refers to the lowest unoccupied molecular orbital of a compound. The term "group" is intended to mean a part of a compound, such as a substituent in an organic compound. The prefix "hetero" indicates that one or more carbon atoms has been replaced with a different atom. The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene" are intended to mean analogous groups having one or more heteroatoms. The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted. The term "arylalkylene" is intended to mean a group derived from an alkyl group having an aryl substituent, which group may be further unsubstituted or substituted. The term "heteroarylalkylene" is intended to mean a group derived from an alkyl group having a heteroaryl substituent, which group may be further unsubstituted or substituted. The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted. The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom. Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "cyclometallated complex" is intended to mean a complex in which an organic ligand is bound to a metal in at least two positions to form a cyclic metal ligand structure, and in which at least one point of attachment is a metal-carbon bond. In addition, the IUPAC numbering system is used throughout, where the groups from the Periodic Table are numbered from left to right as 1 through 18 (CRC Handbook of Chemistry and Physics, 81$^{st}$ Edition, 2000).

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE PREFERRED EMBODIMENTS

Figure 1:
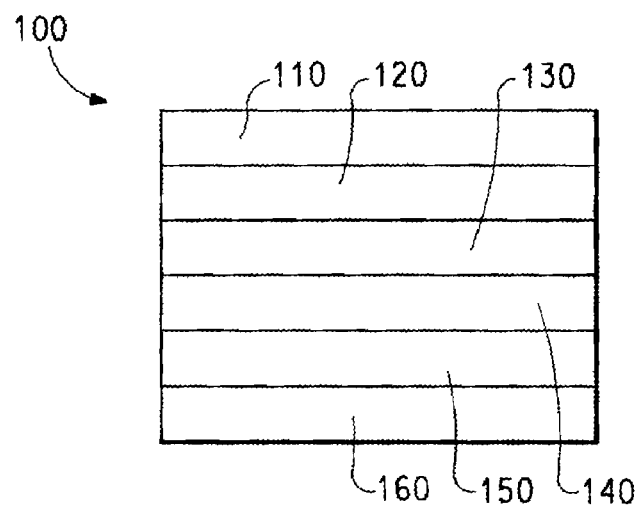
FIG. 1 is a schematic diagram of a light-emitting diode (LED).

The present invention relates to an electronic device comprising at least one electron transport and/or anti-quenching layer and a photoactive layer positioned between two electrodes. The device 100, shown in FIG. 1, has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. As an option, devices frequently use another electron transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary,* 470 and 476 (McGraw-Hill, Inc. 1966). A device within the scope of this invention shall mean a light-emitting diode, light-emitting electroluminescent device, or a photodetector as defined above.

Figure 2:
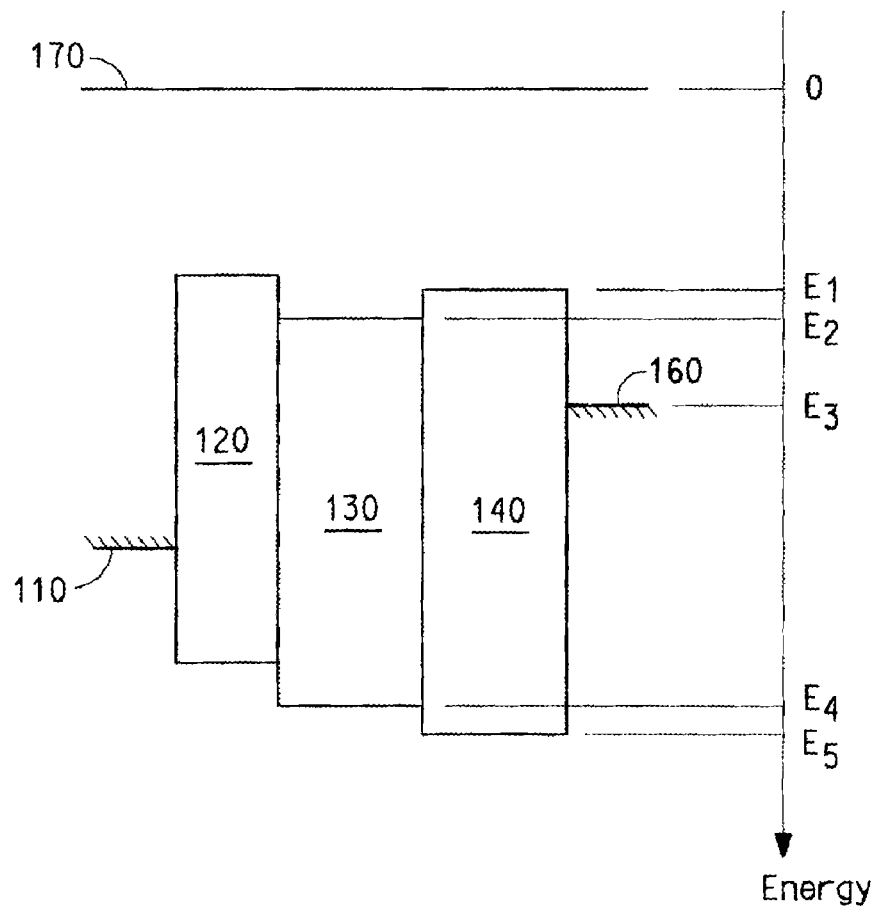
FIG. 2 is a schematic diagram of the energy levels in an LED.
Figure 3A:
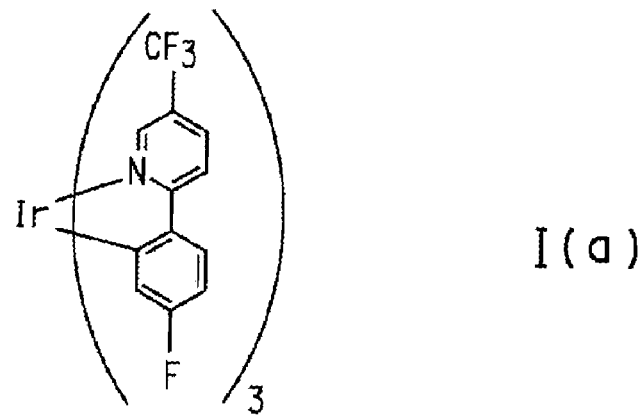
FIG. 3 shows Formulae I(a) through I(e) for electroluminescent iridium complexes.
Figure 3B:
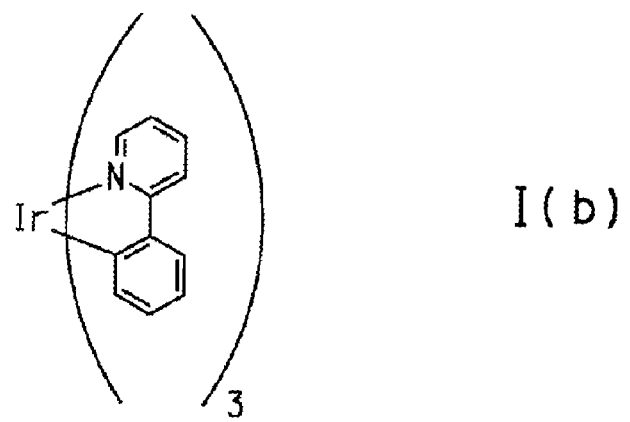
Figure 3C:
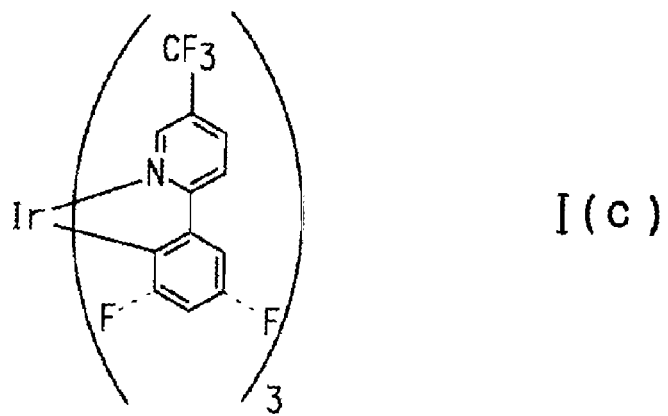
Figure 3D:
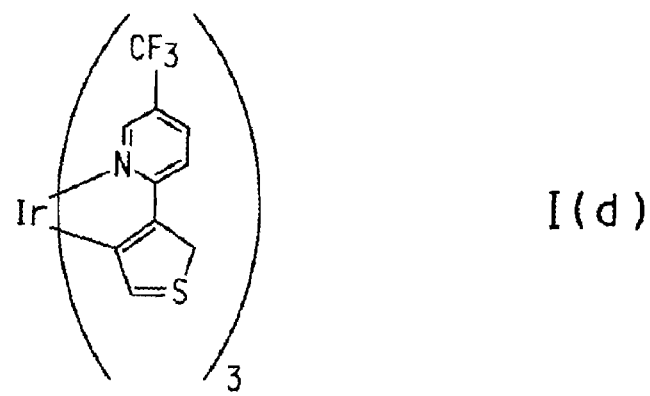
Figure 3E:
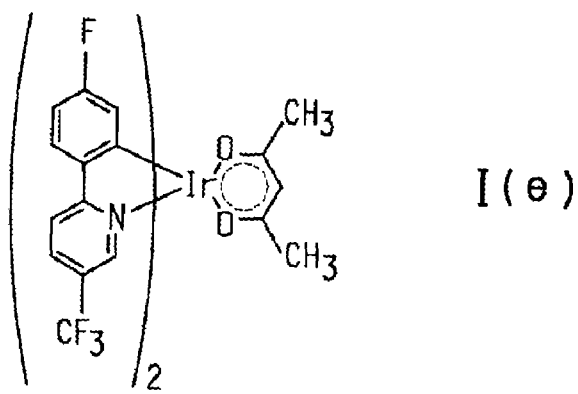

FIG. 2 shows the schematics of the energetics of the devices, which will be used for the discussion below. All of the energy levels are referenced to the vacuum level, 170, with an energy defined to be zero. As such, they are all negative numbers. The lowest un-occupied molecular orbital (LUMO) energy level of the ET/AQ layer is defined as $E_1$. The LUMO of the photoactive layer is defined as $E_2$. The work function of the cathode is defined as $E_3$, the highest occupied molecular orbital (HOMO) of the photoactive layer is defined as $E_4$, and the HOMO of the ET/AQ layer is defined as $E_5$. Higher energy means the energy level is closer to the vacuum level. These energy levels can be measured in the solid state by techniques such as photoelectron spectroscopy. One can also use cyclic voltammetry measurement in solution to measure the relative energy levels of the molecule.

An effective electron transport and/or anti-quenching (ET/AQ) material in an electroluminescent device has to possess the following properties.

1. The material has to be able to transport electrons efficiently, preferably with a mobility of $>10^{-7}$ cm$^2$/(V·sec).

2. The energy difference between the LUMO of the ET/AQ material and the work function of the cathode has to be small enough to allow efficient electron injection from the cathode. The energy barrier is preferred to be less than 1 eV, that is, $E_1-E_3<1$ eV 3. The LUMO level of ET/AQ has to be high enough to prevent it from receiving an electron from the photoactive layer. This usually requires $E_1-E_2>-1$ eV. Preferably, $E_1-E_2>0$.

4. The HOMO level of ET/AQ has to be low enough to prevent it from donating an electron to the photoactive layer. This usually requires $E_4-E_5>-1$ eV. Preferably, $E_4-E_5>0$.

Optimal energy level of ET/AQ in criteria 3 and 4 described above can be determined by the application of electron transfer theory. The rate of electron transfer reaction as a function of the energy difference is described by the Marcus theory. (R. A. Marcus, P. Siders, J. Phys. Chem., 86, 622 (1982). In its simplest form, it is written as $$k=\nu\exp[-(E_f-E_i+\lambda)^2/4\lambda k_B T] \quad (1)$$

Here, k is the rate constant, $k_B$ the Boltzman constant, T the temperature, $E_i$ and $E_f$ are the energies of the initial and final states, and $\lambda$ called the reorganization energy, is a phenomenological parameter describing the collective effects of the vibronic interactions in the initial and final states. The prefactor $\nu$ involves wave function overlap integrals, $\alpha$, and is phenomenologically characterized as depending on the charge separation distance r via $$\nu(r)=\nu_0\exp[-\alpha(r-r_0)] \quad (2)$$

The prefactor $\nu_0$ tends to be universally about $10^{13}$ sec$^{-1}$.

The energy of the final state, that is, the charge separated state, depends on the separation distance of the electron and hole, r, as well as the applied electric field, $E_0$. It can be written as $$E_f=E_f^\infty-e^2/(\in r)-E_0 z \quad (3)$$

where $E_f^\infty$ is the energy of the charge separated state in the absence of an external field and with infinite separation of the electron and hole, $\in$ is the dielectric constant of the medium, and z is the direction of the applied field. How to calculate the electron transfer rate under applied field and variable electron hole distance has been discussed before by Wang and Suna, J. Phys. Chem., 101, 5627-5638 (1997).

In criteria 3, to prevent significant electron transfer quenching to occur, the LUMO level of the ET/AQ layer has to be high enough such that the electron transfer rate from the photoactive layer to the ET/AQ layer is significantly less than the excited state radiative decay rate of the exciton. So the optimal location of the LUMO level depends on the reorganization energy $\lambda$ and overlap integral $\alpha$ of the electron transfer reaction involved, and the radiative lifetime of the exciton of the photoactive layer. Typically, this requires $E_1-E_2>-1$ eV. Preferably, $E_1-E_2>0$.

In criteria 4, similarly, the HOMO level of the ET/AQ layer has to be low enough such that the electron transfer rate from the ET/AQ layer to the luminescent layer is significantly less than the excited state radiative decay rate of the exciton. The optimal location of the HOMO level depends on the reorganization energy $\lambda$ and overlap integral $\alpha$ of the electron transfer reaction involved, and the radiative lifetime of the exciton of the photoactive layer. This usually requires $E_4-E_5>-1$ eV. Preferably, $E_4-E_5>0$.

For any given photoactive material, there is therefore an optimal ET/AQ material to use which fulfills the requirement outlined in criteria 1 to 4. For a series of structurally similar ET/AQ materials, where the reorganization energy and overlap integral are expected to be similar, one expects to find a correlation between the efficiency of the device and the LUMO energy of the ET/AQ material. For a given photoactive material, there should be an optimal range of the LUMO energies of ET/AQ material where the maximal efficiency is achieved.

It is also to be understood that the ET/AQ material has to be chemically compatible with the photoactive material used. For example, the ET/AQ material has to form a smooth film when deposited on the photoactive material layer. If aggregation occurs, the performance of the device will deteriorate. The occurrence of aggregation can be detected by various known techniques in microscopy and spectroscopy.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477-479 (11 Jun. 1992). At least one of the anode and cathode should be at least partially transparent to allow the generated light to be observed.

Examples of hole transport materials which may be used for layer 120 have been summarized, for example, in Kirk-Othmer Encyclopedia of Chemical Technology, Fourth Edition, Vol. 18, p. 837-860, 1996, by Y. Wang. Both hole transporting molecules and polymers can be used. The compound bis(4-N,N-diethylamino-2-methylphenyl)-4-methylphenylmethane (MPMP) has been disclosed to be a suitable hole transport composition in Petrov et al., Published PCT application WO 02/02714. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N, N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline and mixtures thereof. It is also possible to obtain hole transporting polymers by doping hole transporting molecules such as those mentioned above into polymers such as polystyrene and polycarbonate.

Examples of the photoactive layer 130 include all known electroluminescent materials. Organometallic electroluminescent compounds are preferred. The most preferred compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. as have been Examples of a few suitable iridium complexes are given in FIG. 3, as Formulae I(a) through I(e). Analogous tetradentate platinum complexes can also be used. These electroluminescent complexes can be used alone, or doped into charge-carrying hosts, as noted above.

Figure 4:
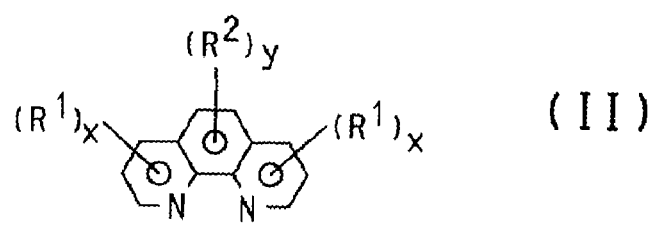
FIG. 4 shows Formula II for an electron transport composition.
Figure 5A:
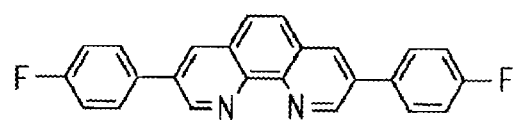
FIG. 5 shows Formulae II(a) through II(i) for an electron transport composition.
Figure 5B:
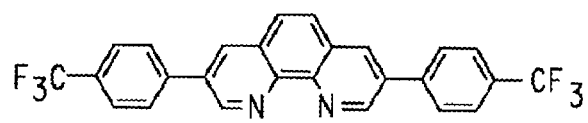
Figure 5C:
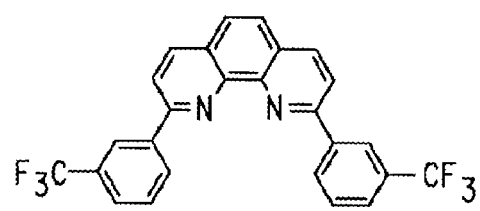
Figure 5D:
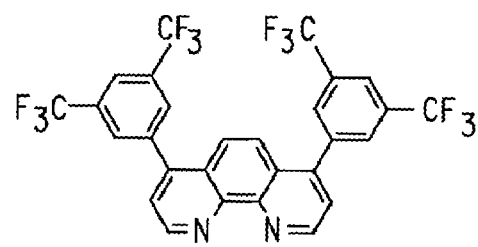
Figure 5E:
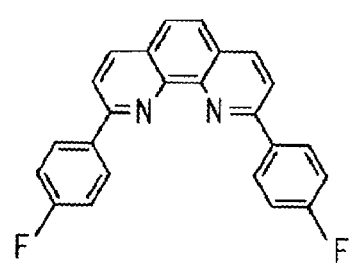
Figure 5F:
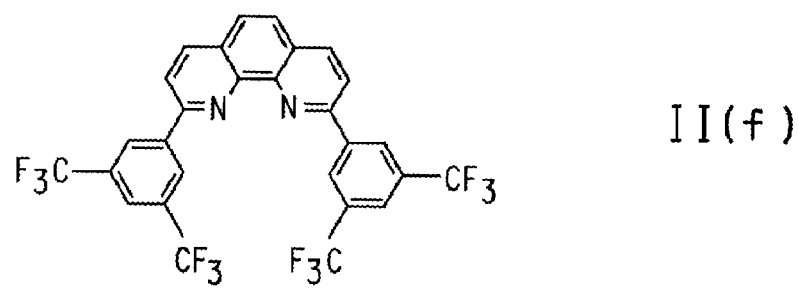
Figure 5G:
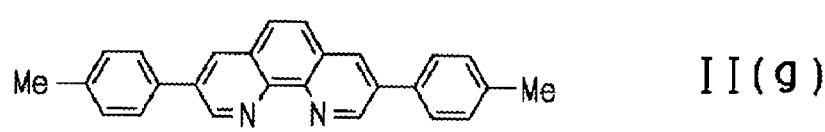
Figure 5H:
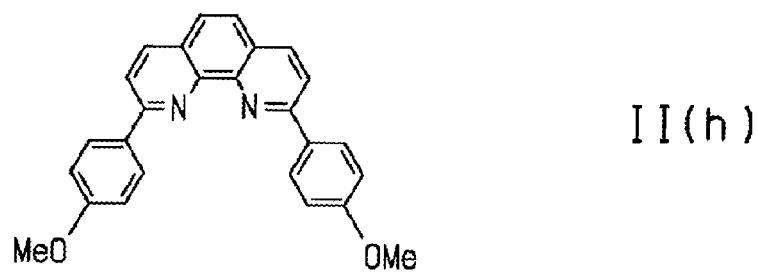
Figure 5I:
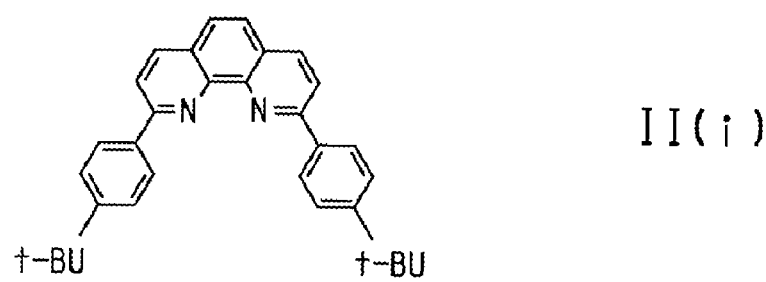

One type of ET/AQ material is a phenanthroline derivative. The phenanthroline derivative can have Formula II, shown in FIG. 4, wherein:

$R^1$ and $R^2$ are the same or different at each occurrence and are selected from H, F, Cl, Br, alkyl, heteroalkyl, alkenyl, alkynyl, aryl, heteroaryl, $C_nH_aF_b$, $OC_nH_aF_b$, $C_6H_cF_d$, and $OC_6H_cF_d$;

a, b, c, and d are each an integer such that $a+b=2n+1$, and $c+d=5$, n is an integer;

x is an integer from 0 through 3;

y is 0, 1 or 2;

with the proviso that there is at least one substituent on an aromatic group selected from F, $C_nH_aF_b$, $OC_nH_aF_b$, $C_6H_cF_d$, and $OC_6H_cF_d$. Specific examples of such phenanthrolines are Formulae II(a) through II(i) in FIG. 5.

Figure 6A:
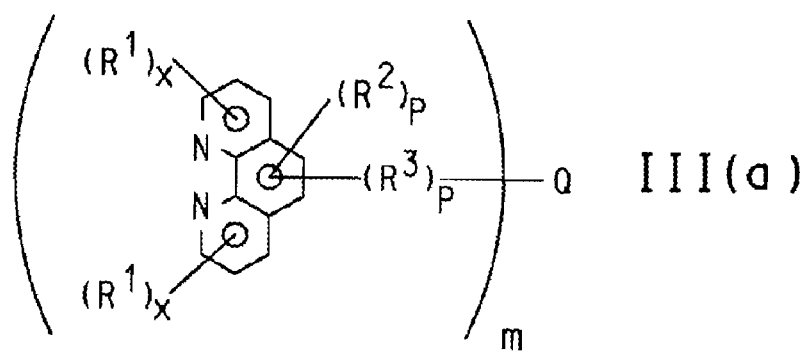
FIG. 6 shows Formulae III(a) and III(b) for an electron transport composition.
Figure 6B:
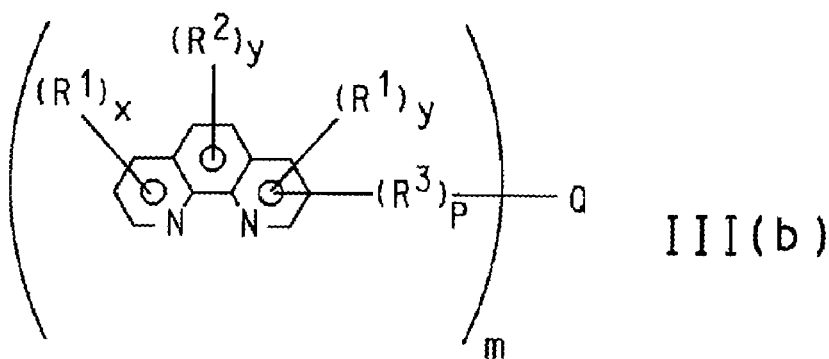
Figure 7A:
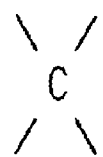
FIG. 7 shows Formulae IV(a) through IV(h) for a multidentate linking group.
Figure 7B:
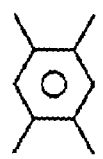
Figure 7C:
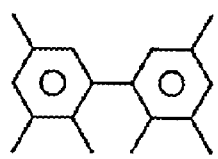
Figure 7D:
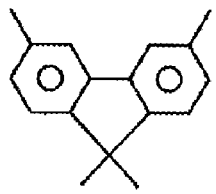
Figure 7E:
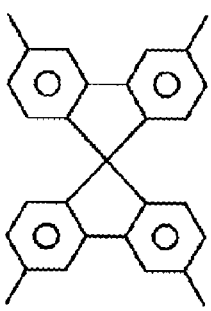
Figure 7F:
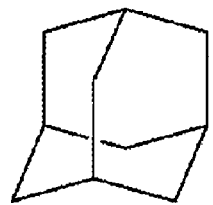
Figure 7G:
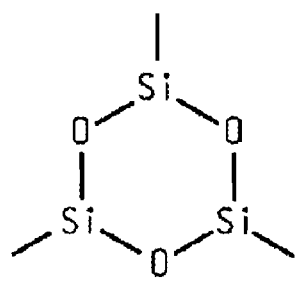
Figure 7H:
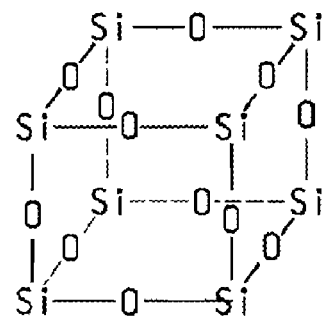

The phenanthroline derivative can have Formulae III(a) or II(b), shown in FIG. 6, wherein:

$R^1$, $R^2$, a through d, n and x are as defined above;

$R^3$ is the same or different at each occurrence and is selected from a single bond and a group selected from alkylene, heteroalkylene, arylene, heteroarylene, arylenealkylene, and heteroarylenealkylene;

Q is selected from a single bond and a multivalent group;

m is an integer equal to at least 2; and p is 0 or 1.

Examples of multivalent Q groups are shown as Formulae IV(a) through IV(h) in FIG. 7.

Figure 8:
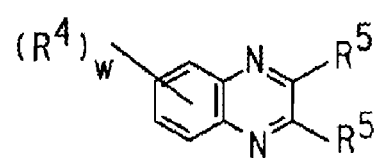
FIG. 8 shows Formula V for an electron transport composition.
Figure 9A:
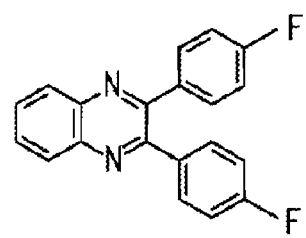
FIG. 9 shows Formulae V(a) through V(ag) for an electron transport composition.
Figure 9B:
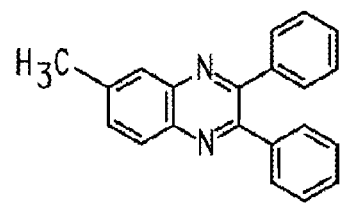
Figure 9C:
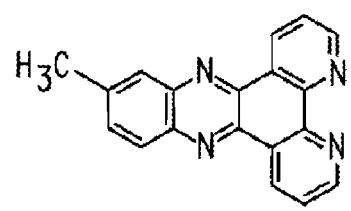
Figure 9D:
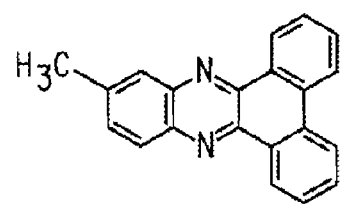
Figure 9E:
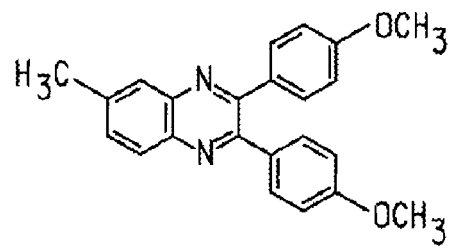
Figure 9F:
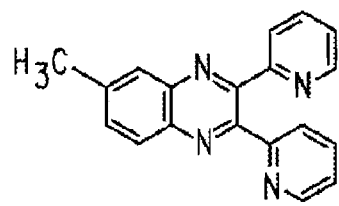
Figure 9G:
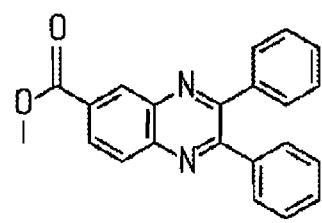
Figure 9H:
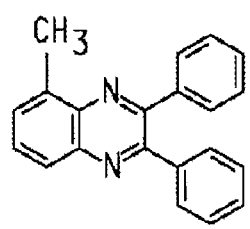
Figure 9I:
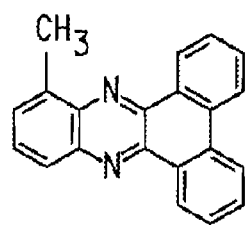
Figure 9J:
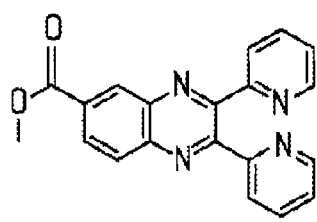
Figure 9K:
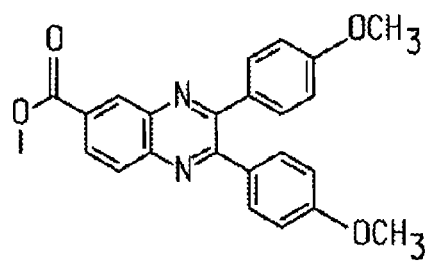
Figure 9L:
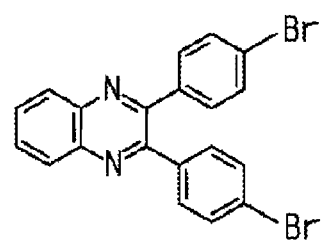
Figure 9M:
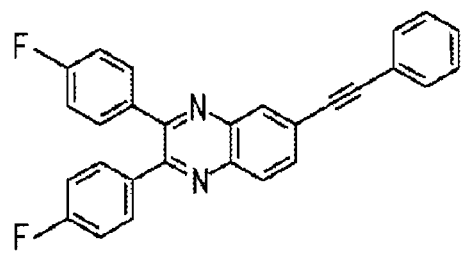
Figure 9N:
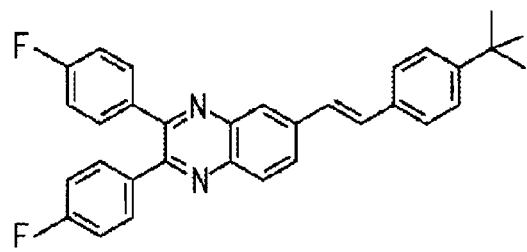
Figure 9O:
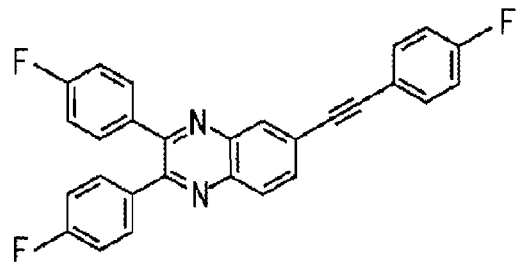
Figure 9P:
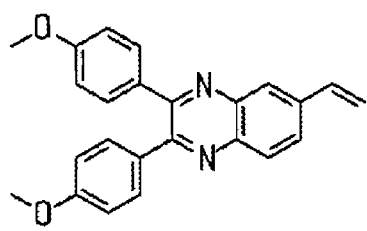
Figure 9Q:
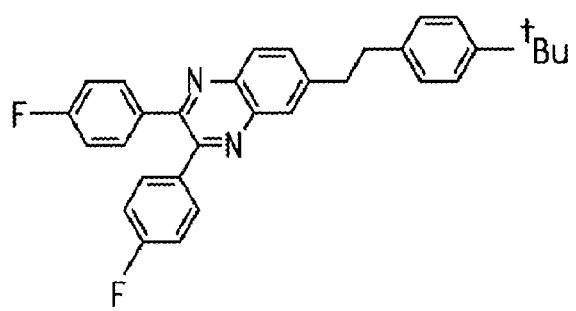
Figure 9R:
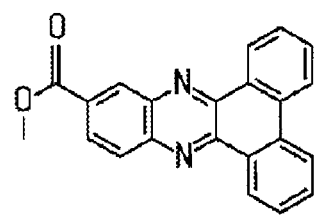
Figure 9S:
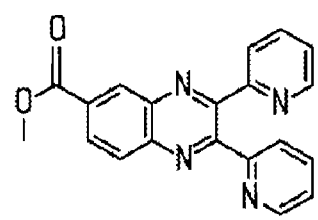
Figure 9T:
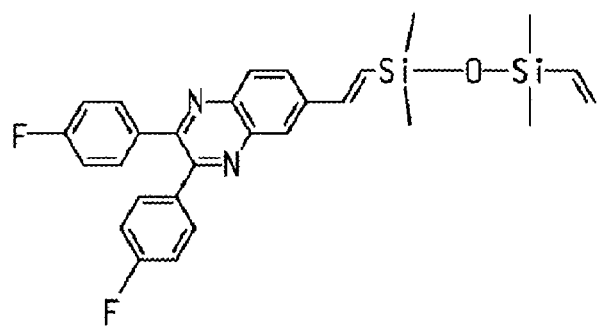
Figure 9U:
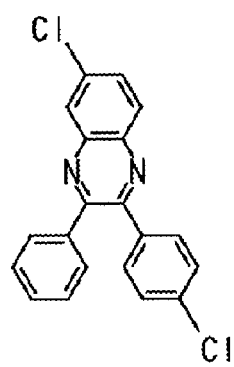
Figure 9V:
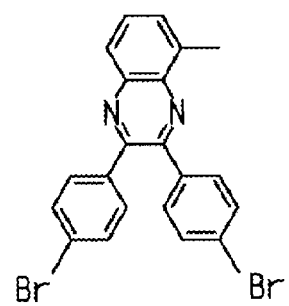
Figure 9W:
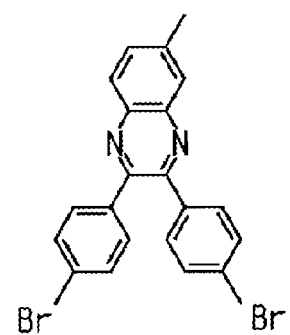
Figure 9X:
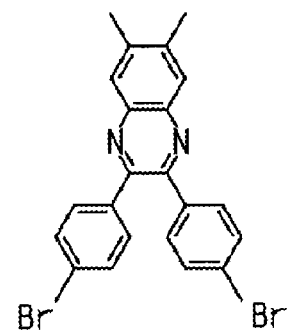
Figure 9Y:
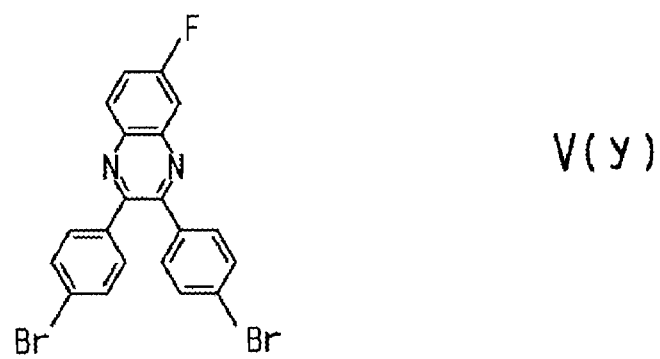
Figure 9Z:
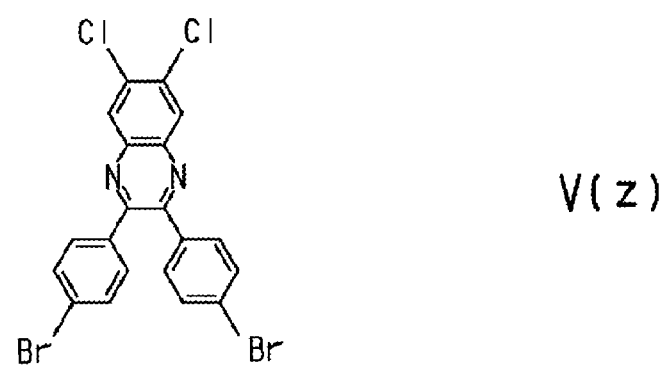
Figure 9A:
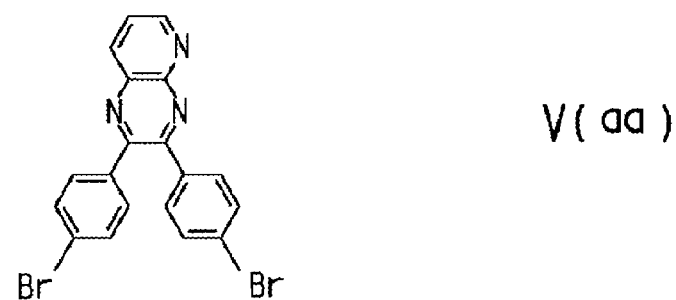
Figure 9A:
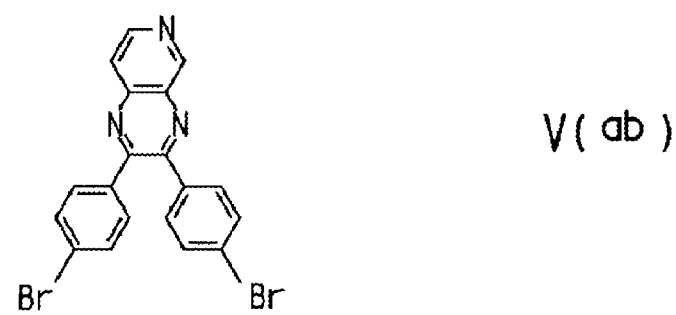
Figure 9A:
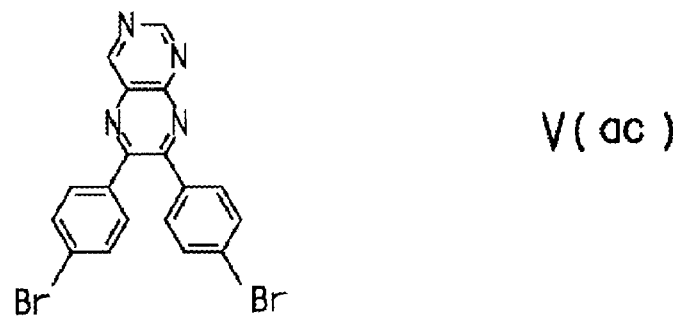
Figure 9A:
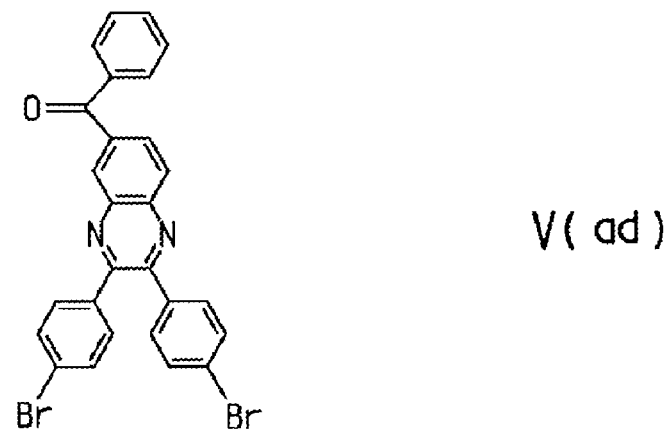
Figure 9A:
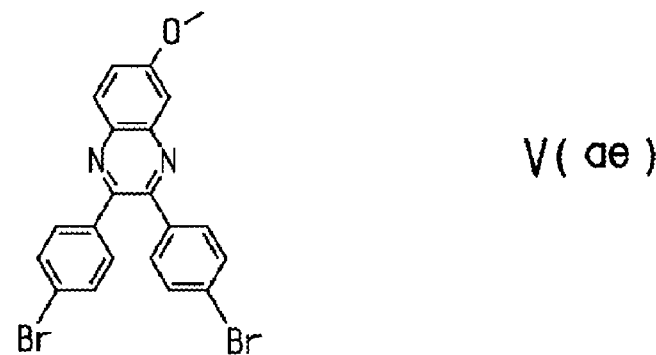
Figure 9A:
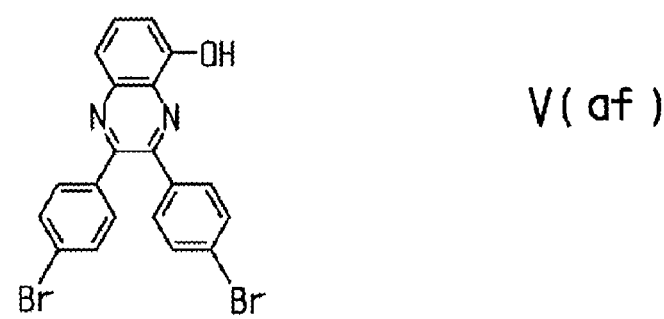
Figure 9A:
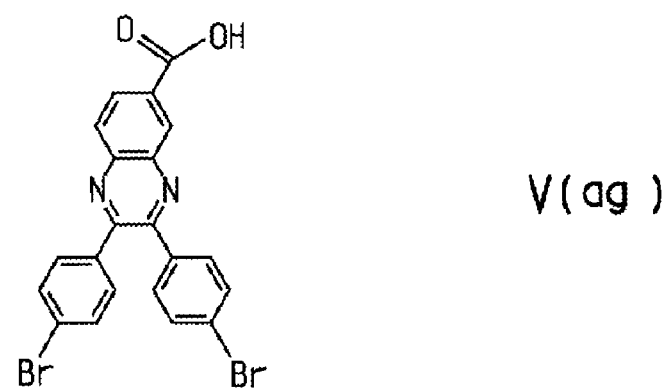

Another type of ET/AQ material is a quinoxaline derivative. The quinoxaline derivative can have Formula V, shown in FIG. 8, wherein:

$R^4$ and $R^5$ are the same or different at each occurrence and are selected from H, F, Cl, Br, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$, or both of $R^5$ together may constitute an arylene or heteroarylene group;

a, b, c, and d are 0 or an integer such that $a+b=2n+1$, and $c+d=5$, n is an integer, and w is 0 or an integer from 1 through 4.

Specific examples of quinoxalines of this formula are given as Formulae V(a) through V(ag) in FIG. 9.

Figure 10:
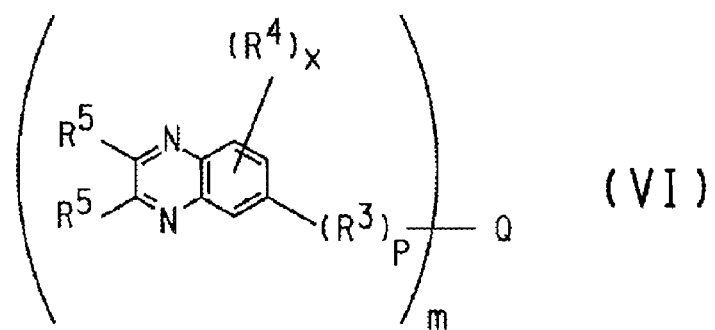
FIG. 10 shows Formula VI for an electron transport composition.

The quinoxaline can have Formula VI, shown in FIG. 10, wherein:

$R^4$, $R^5$, a through d, and n are as defined above, $R^3$ is the same or different at each occurrence and is selected from a single bond and a group selected from alkylene, heteroalkylene, arylene, heteroarylene, arylenealkylene, and heteroarylenealkylene;

Q is selected from a single bond and a multivalent group;

m is an integer equal to at least 2;

p is 0 or 1; and w is 0 or an integer from 1 through 4.

Examples of Q groups are discussed above. Specific examples of quinoxalines of this formula are Formulae VI(a) through VI(m), shown in FIG. 11.

Figure 12:
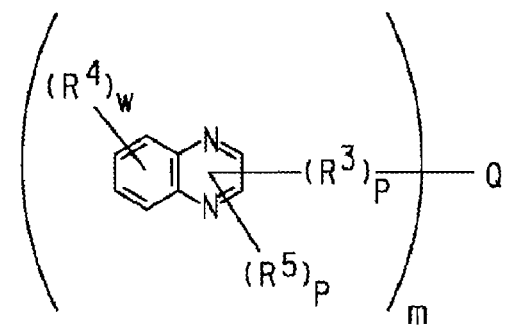
FIG. 12 shows Formula VII for an electron transport composition.

The quinoxaline can have Formula VII, shown in FIG. 12, where $R^3$, $R^4$, $R^5$, Q, a through d, m, n, p and w are as defined above, Examples of additional electron transport materials which can be used in layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating or printing technique, including but not limited to spin-coating, dip-coating, roll-to-roll techniques, ink-jet printing, gravure printing, and screen printing. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layer 140 and 150, 50-2000 Å, preferably 100-1000 Å; cathode 160, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

EXAMPLES

The following examples illustrate certain features and advantages of the present invention. They are intended to be illustrative of the invention, but not limiting. All percentages are by weight, unless otherwise indicated.

Examples 1-17

These examples illustrate the preparation of some ET/AQ compositions.

Example 1

This example illustrates the preparation of Compound V(b) in FIG. 9.

A mixture of 3,4-diaminotoluene (28.78 g, 0.236 mol) and benzil (45 g, 0.214 mol) was refluxed in 738 ml chloroform with 2.16 ml trifluoroacetic acid for 3 hours. The mixture was washed 3 times with 10% HCl, brine, and dried over $MgSO_4$, filtered, and then filtered through a silica bed with vacuum. The resultant solution was evaporated to dryness. Recrystallized 69 grams of crude product from 550 ml methanol. Filtered solids were dried in a vacuum oven at 50° C. for 1 hour to yield 55.56 g of dried solid. 78.8% yield Example 2

This example illustrates the preparation of Compound V(e) in FIG. 9.

A mixture of 3,4-diaminotoluene (4.49 g, 0.037 mol) and 4,4'-dimethoxybenzil (9.46 g, 0.035 mol) was refluxed in 125 ml chloroform with 0.35 ml trifluoroacetic acid for 6 hours. The mixture was washed 2 times with water, dried over $MgSO_4$, and evaporated to ~11 grams. The solid was dissolved in 1:1 ethyl acetate:chloroform for flash chromatography and eluted with ethyl acetate. Evaporated to 9.7 grams of dark solid. 72% yield Example 3

This example illustrates the preparation of Compound V(d) in FIG. 9.

A mixture of 3,4-diaminotoluene (5.36 g, 44 mmol) and phenanthrene quinone (8.33 g, 0.040 mol) was refluxed in 119 ml chloroform with 0.4 ml trifluoroacetic acid for 6 hours. The mixture was filtered through a medium frit and recrystallized from 430 g of methyl ethyl ketone to yield 5.5 g fluffy wool-like, yellow product. 46% yield Example 4

This example illustrates the preparation of Compound V(f) in FIG. 10.

A mixture of 3,4-diaminotoluene (5.36 g, 44 mmol) and 2,2'-Pyridil (8.49 g, 40 mmol) was refluxed in 119 ml chloroform with 0.4 ml trifluoroacetic acid for 4 hours. The reaction mixture was separated and washed 4 times with 100 ml water, and evaporated to 10.4 grams. The resultant solid was dissolved in 1:1 ethyl acetate:chloroform for flash chromatography and eluted with ethyl acetate. Evaporated to yield 9.3 grams of solid.

Example 5

This example illustrates the preparation of Compound V(g) in FIG. 10.

A mixture of methyl-3,4-diaminobenzoate (7.28 g, 44 mmol) and benzil (8.41 g, 40 mmol) was refluxed in 140 ml methylene chloride for 21 hours. The reaction mixture was evaporated to dryness and then dissolved in 520 ml methanol and 150 ml methylene chloride at reflux. The solution was then partially evaporated to selectively crystallize the desired product Example 6

This example illustrates the preparation of Compound V(k) in FIG. 10.

A mixture of Methyl-3,4-diaminobenzoate (6.37 g, 0.038 mol) and 4,4'-dimethoxybenzil (9.46 g, 0.035 mol) was refluxed in 142 ml methylene chloride with 3 drops trifluoroacetic acid for 5 hours. 10.7 g N-methylpyrrolidinone was added and reflux continued for 26 more hours. The mixture was washed 3 times with water, dried over $MgSO_4$, filtered and then precipitated the product be decanting the organic solution into 550 g methanol. After standing overnight, the product was filtered and dried at 95° C. in vacuum to yield 10.39 g product.

Example 7

This example illustrates the preparation of Compound V(r) in FIG. 10.

A mixture of Methyl-3,4-diaminobenzoate (6.12 g, 0.037 mol) and phenanthrene quinone (7.08 g, 0.034 mol) was refluxed in 119 ml methylene chloride. 100 grams of N-methylpyrrolidinone was added and the chlorinated solvent was distilled out. The pot was warmed to 150° C. whereupon a clear solution was obtained and the reaction was tracked by gas chromatography. The product was precipitated by pouring into 410 g methanol and the solid precipitate filtered off. The product was recrystallized from toluene then recrystallized again from a combination of methyl ethyl ketone 1200 g, toluene 150 g, and tetrahydrofuran 1100 g. Yield was 3.3 grams of pearly golden wool-like material.

Example 8

This example illustrates the preparation of Compound V(I) in FIG. 10.

A mixture of 1,2-phenylenediamine (13.91 g, 0.129 mol) and 4,4'-dibromobenzil (45, 0.116 mol) was refluxed in 558 ml chloroform with 1.0 ml trifluoroacetic acid for 6 hours. The mixture was washed 3 times with 10% HCl, and evaporated to ~51 grams. Recrystallized from 600 ml ethyl acetate with 100 ml methanol at reflux. Large crystals formed overnight and were filtered and washed with methanol twice and dried to 29.63 g with a 4.9 g second crop from the chilled mother liquor.

Example 9

This example illustrates the preparation of Compound V(h) in FIG. 10.

A mixture of 2,3-diaminotoluene (4.84 g, 0.040 mol) and benzil (7.56 g, 0.036 mol) was refluxed in 112 ml methylene chloride for 19 hours. The mixture was washed 4 times with 12% HCl, and dried over $MgSO_4$ filtered and evaporated to ~9.5 grams of brown solid. The solid was dissolved into 495 g methanol at reflux and then ~300 g solvent was distilled out. Cooling with ice yielded nice crystals. Filtered and washed crystal cake with methanol.

Example 10

This example illustrates the preparation of Compound V(i) in FIG. 9.

A mixture of 2,3-diaminotoluene (5.05 g, 0.041 mol) and phenanthrenequinone (7.84 g, 0.038 mol) were refluxed in 112 ml chloroform for 29 hours. The resultant solution was chromatographed down a silica column with chloroform eluant. Evaporated product from solvent to yield about 10 grams before vacuum oven drying. Material appeared crystalline Example 11

This example illustrates the preparation of Compound V(j) in FIG. 9.

A mixture of methyl-3,4-diaminobenzoate (7.28 g, 0.044 mol) and 2,2'-pyridil (8.48 g, 0.040 mol) was refluxed in 140 ml methylene chloride for 7 hours. The solution was evaporated to 15.7 grams and the solid dissolved in 240 ml methylene chloride and 140 ml methanol at reflux. After addition of 280 ml methanol and evaporation of ~150 ml of the solvent the solution was left to stand overnight. The resulting solid was collected and dried to 9.8 grams. Took 7.7 g material and dissolved in 203 g methanol with 50 g methylene chloride. Distilled off >50 ml of solvent. Crystals formed overnight. Filtered and dried in vacuum oven.

Example 12

Figure 11A:
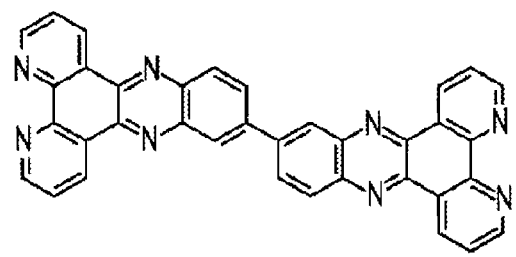
FIG. 11 shows Formulae VI(a) through VI(k) for an electron transport composition.
Figure 11B:
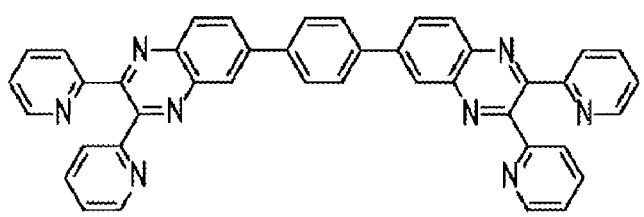
Figure 11C:
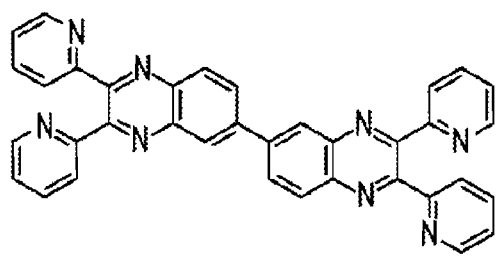
Figure 11D:
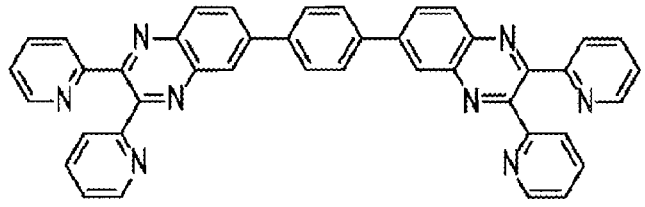
Figure 11E:
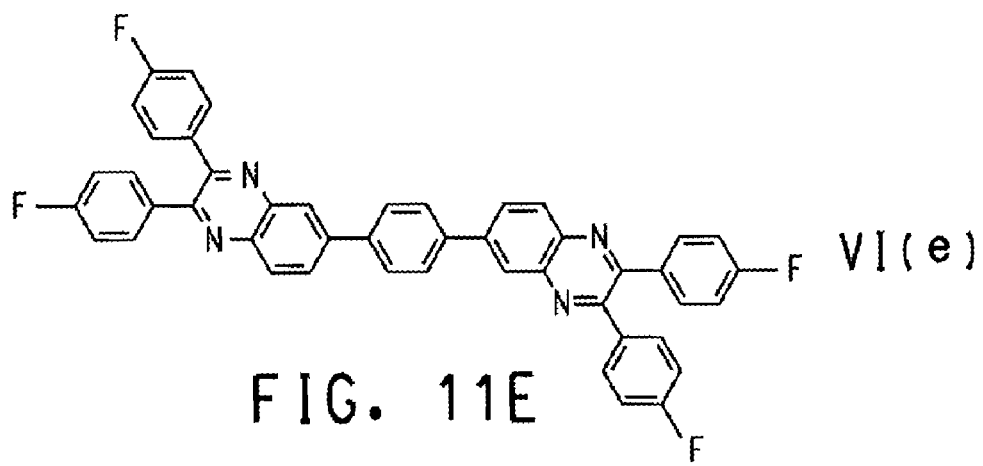
Figure 11F:
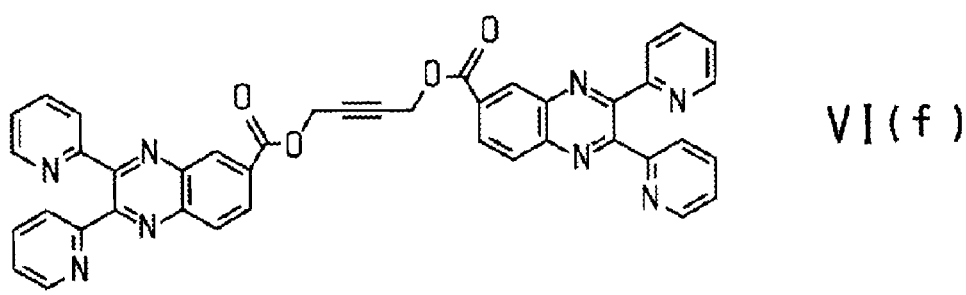
Figure 11G:
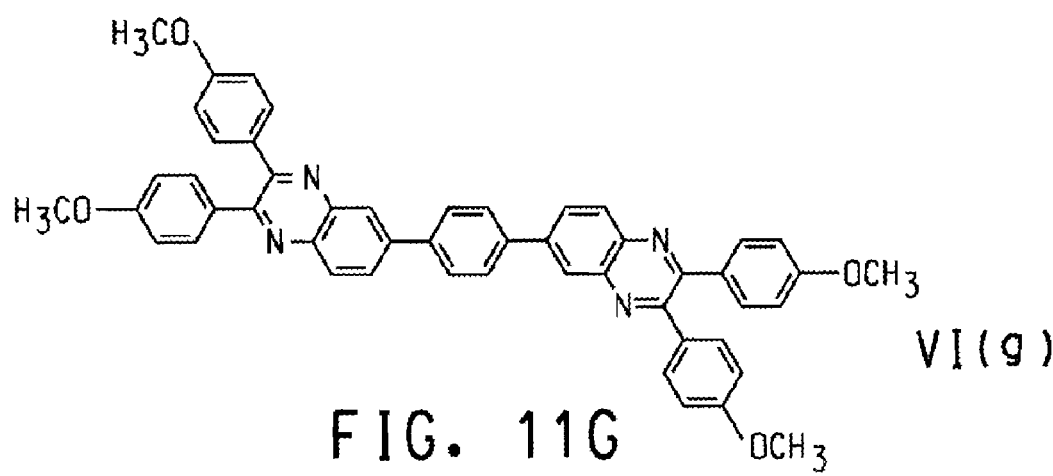
Figure 11H:
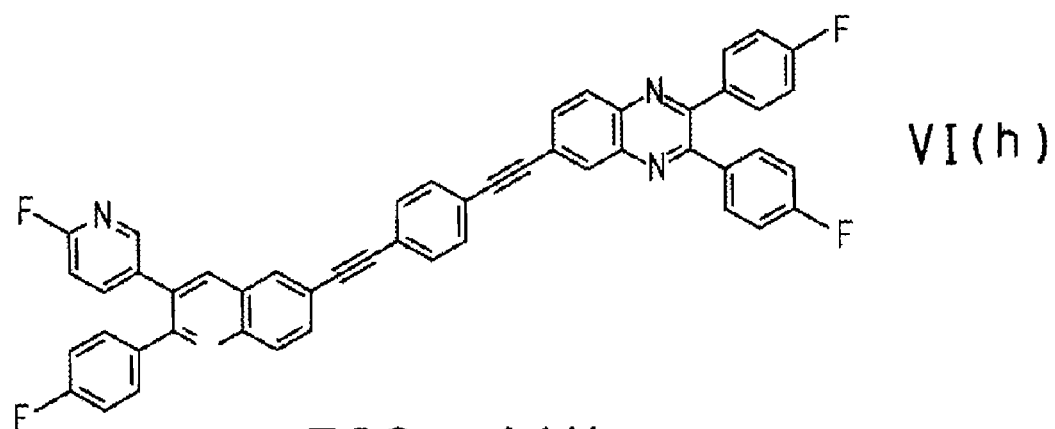
Figure 11I:
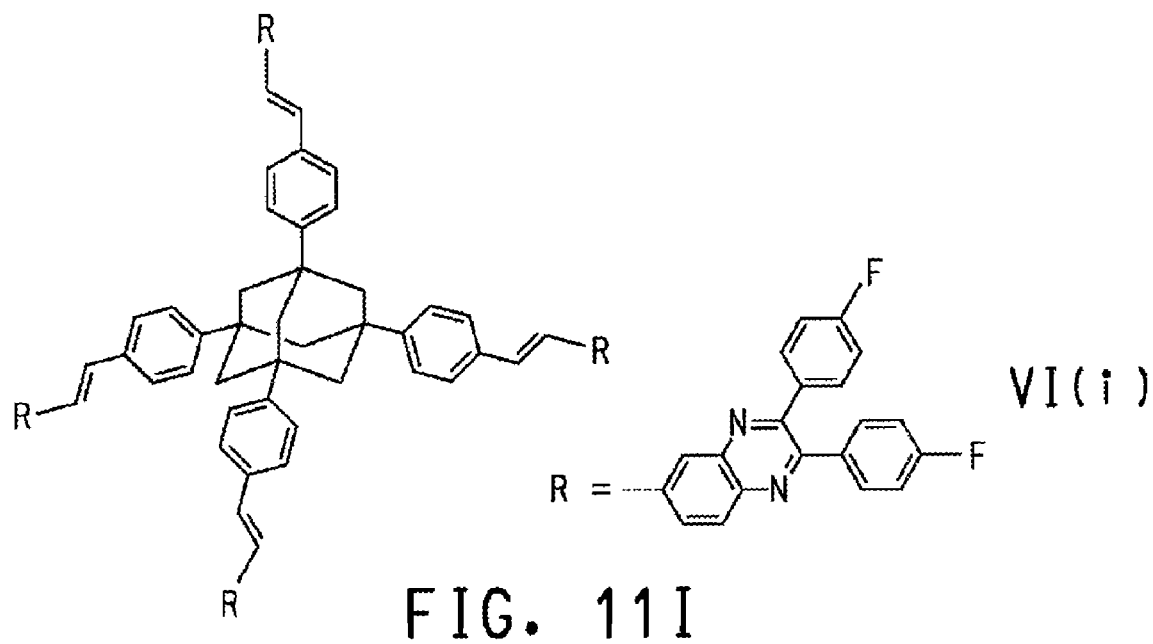
Figure 11J:
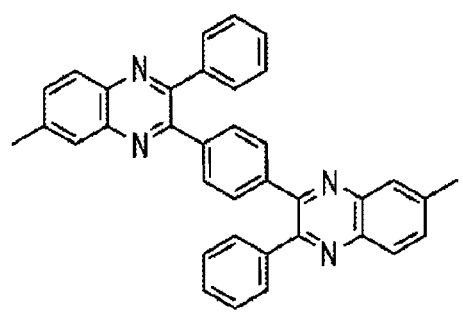
Figure 11K:
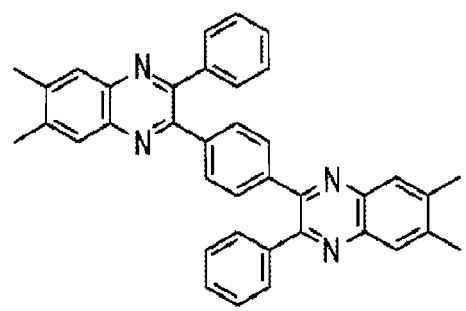

This example illustrates the preparation of Compound VI(a) in FIG. 11A.

A mixture of 3,3-diaminobenzidine (0.4580 g, 2.14 mmol) and 1,10-phenanthroline-5,6-dione (0.9458 g, 4.5 mmol) were heated at 85° C. in 10 g n-methylpyrrolidinone with 0.045 ml trifluoroacetic acid for 23 hours. At ambient temperature chloroform was charged to pot and contents were filtered through a fine frit and washed with acetone, and diethylether then dried at 90° C. and vacuum.

Example 13

This example illustrates the preparation of Compound II(c) in FIG. 5.

A mixture of 2,9-diiodo-1,10-phenanthroline (900 mg, 2.08 mmol, prepared according to: Toyota et al. *Tetrahedron Letters* 1998, 39, 2697-2700), 3-trifluoromethylbenzeneboronic acid (989 mg, 5.20 mmol, Aldrich Chemical Company, Milwaukee, Wis.), tetrakistriphenylphosphine palladium (481 mg, 0.416 mmol, Aldrich Chemical Company), and sodium carbonate (882 mg, 8.32 mmol) were allowed to reflux in water (20 mL)/toluene (50 mL) for 15 h under nitrogen. Then the organic layer was separated, and the aqueous layer extracted with 3×25 mL of chloroform. The organic layers were combined, dried with sodium sulfate, and evaporated to dryness. Purification was accomplished by silica gel flash chromatography with hexanes/dichloromethane (1:1, v:v) as the eluent (product $R_f$=0.25), to afford the desired product, >95% pure by $^1$H NMR, as a pale yellow solid (560 mg, 57%). $^1$H NMR (CDCl$_3$, 300 MHz, 296 K): δ 8.81 (s, 2H), 8.63 (d, 2H, J=7.5 Hz), 8.36 (d, 2H, J=8.4 Hz), 8.19 (d, 2H, J=8.41 Hz), 7.84 (s, 2H), 7.68-7.77 (m, 6H) ppm. $^{19}$F NMR (CDCl$_3$, 282 MHz, 296 K) δ−63.25 ppm.

Compounds II(a), II(g), II(h) and II(i) were made using an analogous procedure.

Example 14

This example illustrates the preparation of Compound II(b) in FIG. 5.

The same procedure was used as in Example 13, with 3,8-dibromo-1,10-phenanthroline (1.5 g, 4.4 mmol, prepared according to: Saitoh et al. *Canadian Journal of Chemistry* 1997, 75, 1336-1339.), 4-trifluoromethylbenzeneboronic acid (2.11 g, 11.1 mmol, Lancaster Chemical Company, Windham, N.H.), tetrakistriphenylphosphine palladium (513 mg, 0.444 mmol), and sodium carbonate (1.41 g, 13.3 mmol), water (20 mL), and toluene (100 mL). Purification was achieved via silica gel flash chromatography (dichloromethane/methanol, 9:1, v:v), and then by washing the product with cold methanol, to afford a white solid (520 mg, 25%)>95% pure by $^1$H NMR. $^1$H NMR (CDCl$_3$, 300 MHz, 296 K): δ 9.46 (d, 2H, J=2.3 Hz), 8.45 (d, 2H, 2.3 Hz), 7.94 (s, 2H), 7.91 (d, 4H, J=8.3 Hz), 7.82 (d, 4H, J=8.4 Hz) ppm. $^{19}$F NMR (CDCl3, 282 MHz, 296 K) δ−63.12 ppm.

Example 15

This example illustrates the preparation of Compound II(e) in FIG. 5.

2,9-Diiodo-1,10-phenanthroline (1.00 g, 2.31 mmol), 4-fluorobenzeneboronic acid (972 mg, 6.96 mmol), bis (diphenylphosphino)butane (92 mg, 0.23 mmol, Aldrich), palladium acetate (52 mg, 0.23 mmol, Aldrich), and potassium fluoride (810 mg, 13.9 mmol, Aldrich) were allowed to reflux in anhydrous dioxane (100 mL) for 15 h, after which time the dioxane was removed under reduced pressure, and the crude residue was subjected to an aqueous work-up as for Example 1. Purification was achieved via silica gel flash chromatography (dichloromethane, 100% product $R_f$=0.57), to afford a pale yellow solid (567 mg, 67%), >95% pure by $^1$H NMR. $^1$H NMR (CDCl$_3$, 300 MHz, 296 K): δ 8.43 (dd, 4H, $J_{HH}$=10.4 Hz, $J_{HF}$=5.5 Hz), 8.28 (d, 2H, J=8.4 Hz), 7.77 (s, 2H), 7.26 (dd, 4H, $J_{HH}$=9.9 Hz, $J_{HF}$=5.9 Hz) ppm. $^{19}$F NMR (CDCl3, 282 MHz, 296 K) δ−113.0 ppm.

Example 16

This example illustrates the preparation of Compound II(d) in FIG. 5.

The same procedure was used as in Examples 13 and 14, using 4,7-dichloro-1,10-phenanthroline (300 mg, 1.20 mmol, prepared according to: *J. Heterocyclic Chemistry* 1983, 20, 681-6), 3,5-bis(trifluoromethyl)benzeneboronic acid (0.930 mg, 3.60 mmol, Aldrich), bis(diphenylphosphino)butane (154 mg, 0.361 mmol), palladium acetate (81 mg, 0.361 mmol), sodium carbonate (0.510 mg, 9.62 mmol), water (5 mL), and toluene (30 mL), to afford the desired product as a white solid (410 mg, 56%). $^1$H NMR (CDCl$_3$, 300 MHz, 296 K): δ 9.35 (d, 2H, J=4.49 Hz), 8.06 (s, 2H), 8.00 (s, 4H), 7.73 (2H, s), 7.66 (d, 2H, J=4.52 Hz) ppm. $^{19}$F NMR (CDCl$_3$, 282 MHz, 296 K) δ−63.32 ppm.

Example 17

This example illustrates the preparation of Compound II(f) in FIG. 5.

The same procedure was used as in Example 15, using 2,9-dichloro-phenanthroline (1.0 g, 4.01 mmol, prepared according to: Yamada et al. *Bulletin of the Chemical Society of Japan* 1990, 63, 2710-12), 3,5-bistrifluoromethylbenzeneboronic acid (2.59 g, 10.0 mmol), bis(diphenylphosphino) butane (171 mg, 0.401 mmol), palladium acetate (90 mg, 0.401 mmol), and potassium fluoride (1.40 g, 24.1 mmol), and anhydrous dioxane (100 mL). The product was purified by washing the crude material with diethyl ether, to afford the desired product as a white solid (345 mg, 14%). $^1$H NMR (CDCl$_3$, 300 MHz, 296 K): δ 8.92 (d, 4H, $J_{HF}$=1.46 Hz), 8.45 (d, 2H, J=8.3 Hz), 8.25 (d, 2H, J=8.5 Hz), 8.02 (s, 2H), 7.91 (s, 2H) ppm. $^{19}$F NMR (CDCl$_3$, 282 MHz, 296 K) δ−63.50 ppm.

Figure 13A:
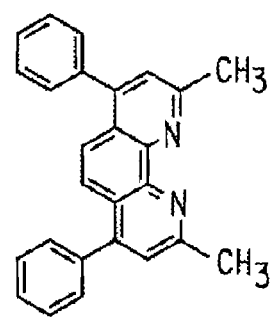
FIG. 13 shows formulae for known electron transport compositions.
Figure 13B:
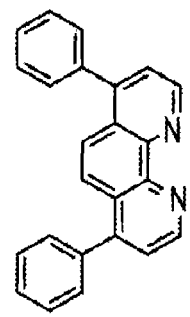

The properties of the electron transport and/or antiquenching compositions are summarized in Table 1 below. Known ET/AQ compounds A and B are shown in FIG. 13.

TABLE 1

| | Properties | | | |
|---|---|---|---|---|
| Compounds | Absorption onset (nm), E1-E5 | Absorption maximum (nm) | $E_{1/2}$ vs SCE (volt), | LUMO vs vacuum (eV), E1 |
| Compound II(b) | 382 | 318 | −1.56 | −3.28 |
| Compound II(a) | 376 | 320 | −1.77 | −3.07 |
| Compound II(c) | 368 | 342 | −1.68 | −3.16 |
| Compound II(d) | 362 | 310 | −1.54 | −3.3 |
| Compound II(e) | 372 | 342 | −1.8 | −3.04 |
| Compound II(f) | 370 | 342 | −1.52 | −3.32 |
| Compound V(a) | 375 | 345 | −1.5 | −3.33 |
| Compound V(b) | 378 | 339 | −1.6 | −3.24 |
| Compound V(c) | 400 | 385 | −1.17 | −3.67 |
| Compound V(d) | 410 | 397 | −1.3 | −3.54 |
| Compound V(g) | 390 | 352 | −1.29 | −3.55 |
| Compound V(a) | — | — | — | — |
| Compound V(e) | 405 | 369 | −1.66 | −3.18 |
| Compound V(f) | 378 | 339 | −1.53 | −3.31 |
| Compound V(k) | 420 | 382 | −1.35 | −3.49 |
| Compound V(i) | 407 | 394 | −1.28 | −3.56 |
| Compound V(h) | 385 | 343 | −1.59 | −3.25 |
| Compound V(r) | 417 | 401 | −1.03 | −3.81 |
| Compound V(l) | 380 | 347 | −1.49 | −3.35 |
| Compound V(j) | 380 | 342 | −1.22 | −3.62 |
| Comp. A DDPA | 368 | 310 | −1.85 | −2.99 |
| Comp. B DPA | 366 | 316 | −1.95 | −2.89 |

Example 18

This example illustrates the preparation of an iridium electroluminescent complex, shown as Formula I(a) in FIG. 3.

Phenylpyridine Ligand,
2-(4-fluorophenyl)-5-trifluoromethylpyridine

The general procedure used was described in O. Lohse, P. Thevenin, E. Waldvogel *Synlett,* 1999, 45-48. A mixture of 200 ml of degassed water, 20 g of potassium carbonate, 150 ml of 1,2-dimethoxyethane, 0.5 g of Pd(PPh$_3$)$_4$, 0.05 mol of 2-chloro-5-trifluoromethylpyridine and 0.05 mol of 4-fluorophenylboronic acid was refluxed (80-90° C.) for 16-30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%.

Iridium Complex:

A mixture of IrCl$_3$.nH$_2$O (54% Ir; 508 mg), 2-(4-fluorophenyl)-5-trifluoromethylpyridine, from above (2.20 g), AgOCOCF$_3$ (1.01 g), and water (1 mL) was vigorously stirred under a flow of N$_2$ as the temperature was slowly (30 min) brought up to 185° C. (oil bath). After 2 hours at 185-190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at −10° C. overnight. The yellow precipitate of the tris-cyclometalated complex, compound b, was separated, washed with methanol, and dried under vacuum. Yield: 1.07 g (82%). X-Ray quality crystals of the complex were obtained by slowly cooling its warm solution in 1,2-dichloroethane.

Iridium complex I(c) was made using an analogous procedure.

Example 19

This example illustrates the preparation of an iridium electroluminescent complex, shown as Formula I(d) in FIG. 3.

Ligand, 2-(2-thienyl)-5-(trifluoromethyl)pyridine 2-thienylboronic acid (Lancaster Synthesis, Inc., 1.00 g, 7.81 mmol), 2-chloro-5-trifluoromethylpyrdine (Adrich Chemical Co., 1.417 g, 7.81 mmol), tetrakistriphenylphosphine palladium(0) (Aldrich, 451 mg, 0.391 mmol), potassium carbonate (EM Science, 3.24 g, 23.4 mmol), water (20 mL), and dimethoxyethane (Aldrich, 20 mL) were allowed to stir at reflux for 20 hours under $N_2$, after which time the mixture was cooled to room temperature and the organic and aqueous layers were separated. The aqueous layer was extracted with 3×50 mL of diethyl ether, and the combined organic fractions were dried with sodium sulfate, filtered, and the filtrate was evaporated to dryness. The crude product was purified by silica gel flash chromatography with $CH_2Cl_2$/hexanes (1:1) as the eluent (product Rf=0.5), to afford the product as a white crystalline solid (yield=5.2 g, 73% isolated yield). $^1$H NMR ($CDCl_3$, 296 K, 300 MHz): δ=7.73-7.57 (2H, m), 7.55 (1H, d, J=8.5 Hz), 7.34 (1H, d, J=4.8 Hz), 6.88 (1H, d, J=4.8 Hz) ppm. $^{19}$F NMR ($CDCl_3$, 296 K, 282 MHz) δ=−62.78 ppm. Intermediate bridged dimer,

[IrCl{2-(2-thienyl)-5-(trifluoromethyl)pyridine}2]2

2-(2-thienyl)-5-(trifluoromethyl)pyridine from above (555 mg, 2.42 mmol), iridium trichloride (Strem Chemicals, 401 mg, 1.13 mmol), 2-ethoxyethanol (Aldrich Chemical Co., 10 mL) and water (1 mL) were allowed to reflux under nitrogen for 15 hours, after which time the reaction was allowed to cool to room temperature. The resulting precipitated product was collected by filtration, washed with hexanes, and dried in vacuo, to afford 575 mg (37%) of the product as a red-orange solid. $^1$H NMR ($CDCl_3$, 296 K, 300 MHz): δ=9.30 (4H, d, J=1.5 Hz), 7.80 (4H, dd, J=2.0 Hz and 8.5 Hz), 7.59 (4H, d, J=8.5 Hz), 7.21 (8H, d, J=4.8 Hz), 5.81 (d, 4H, J=4.9 Hz). $^{19}$F NMR ($CDCl_3$, 282 MHz) δ=−62.07 ppm.

Iridium Complex [Ir{2-(2-thienyl)-5-(trifluoromethyl)pyridine}3]

[IrCl{2-(2-thienyl)-5-(trifluoromethyl)pyridine}2]2 from above (100 mg, 0.073 mmol), 2-(2-thienyl)-5-(trifluoromethyl)pyridine from Example 1 (201 mg, 0.88 mmol), and silver trifluoroacetate (Aldrich, 40 mg, 0.18 mmol) were combined and allowed to stir at 170-180° C. under nitrogen for 10 min. Then the mixture was allowed to cool to room temperature and it was redissolved in a minimum amount dichloromethane. The solution was passed through a silica gel column with dichloromethane/hexanes (1:1) as the eluting solvent. The first red-orange fraction to come down the column (product Rf=0.5) was collected and evaporated to dryness. The residue was suspended in hexanes, and the precipitated product was filtered and washed with excess hexanes to remove any residual 2-(2-thienyl)-5-(trifluoromethyl) pyridine, to afford the product as a red-orange solid. Isolated yield=50 mg (39%). $^1$H NMR ($CDCl_3$, 296 K, 300 MHz): δ=7.73-7.57 (6H, m), 7.55 (3H, d, J=8.5 Hz), 7.34 (3H, d, J=4.8 Hz), 6.88 (3H, d, J=4.8 Hz). $^{19}$F NMR ($CDCl_3$, 296 K, 282 MHz) δ=−62.78.

Example 20

This example illustrates the formation of OLEDs using the charge transport compositions of the invention.

Thin film OLED devices including a hole transport layer (HT layer), electroluminescent layer (EL layer) and at least one electron transport and/or anti-quenching layer (ET/AQ layer) were fabricated by the thermal evaporation technique. The base vacuum for all of the thin film deposition was in the range of $10^{-6}$ torr. The deposition chamber was capable of depositing five different films without the need to break up the vacuum.

Patterned indium tin oxide (ITO) coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to $10^{-6}$ torr. The substrate was then further cleaned using an oxygen plasma for about 5-10 minutes. After cleaning, multiple layers of thin films were then deposited sequentially onto the substrate by thermal evaporation. Finally, patterned metal electrodes of Al or LiF and Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

Figure 14:
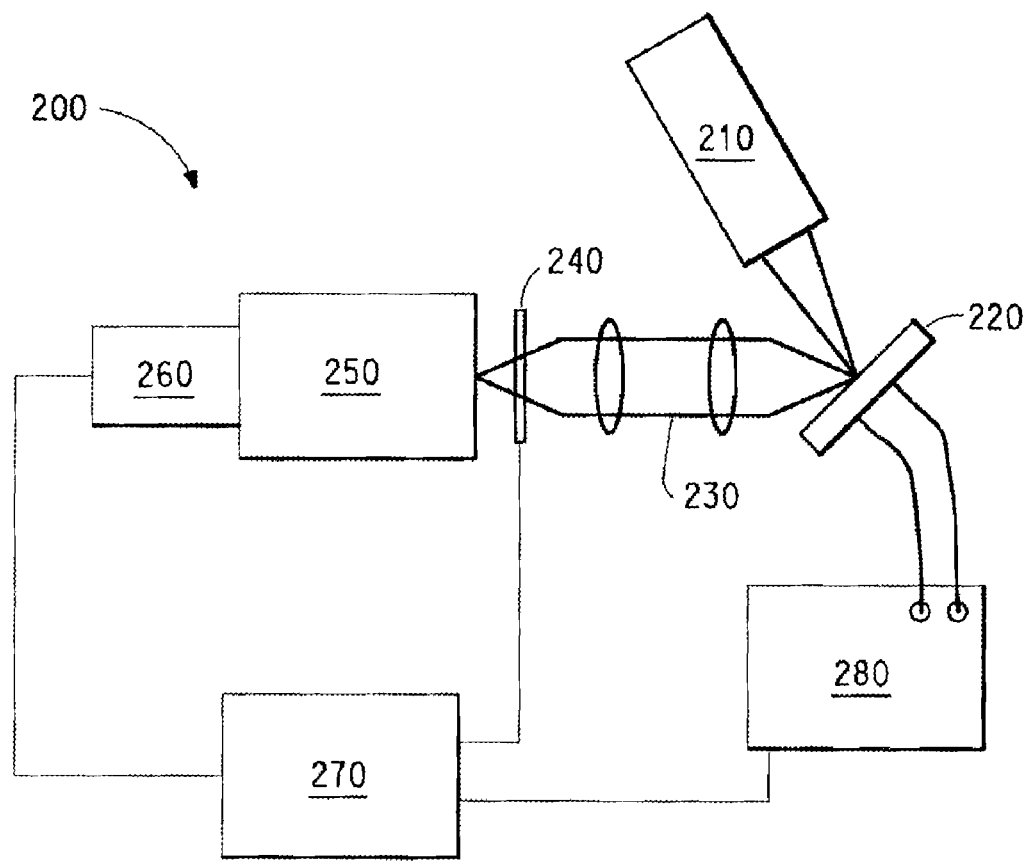
FIG. 14 is a schematic diagram of a testing device for an LED.

The OLED samples were characterized by measuring their (1) current-voltage (I-V) curves, (2) electroluminescence radiance versus voltage, and (3) electroluminescence spectra versus voltage. The apparatus used, 200, is shown in FIG. 14. The I-V curves of an OLED sample, 220, were measured with a Keithley Source-Measurement Unit Model 237, 280. The electroluminescence radiance (in the unit of $Cd/m^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in cd/A.

Iridium compounds XII(b) was made according to the procedure in Appl. Phys. Lett., 1999, 75, 4. The different iridium complexes have the properties given below in Table 2.

TABLE 2

Properties of the Iridium compounds

| EL Compound | $E_{1/2}$ vs SCE, volt | HOMO vs vacuum (eV), E4 | $E_{1/2}$ vs SCE, volt | Absorption onset (nm); E2-E4 | LUMO vs vacuum (eV), E2 |
|---|---|---|---|---|---|
| I(a) | 1.23 | −6.07 | −1.68 | 510 | −3.64 |
| I(b) | 0.72 | −5.56 | −2.21 | 511 | −3.13 |

TABLE 2-continued

Properties of the Iridium compounds

| EL Compound | $E_{1/2}$ vs SCE, volt | HOMO vs vacuum (eV), E4 | $E_{1/2}$ vs SCE, volt | Absorption onset (nm); E2-E4 | LUMO vs vacuum (eV), E2 |
|---|---|---|---|---|---|
| I(c) | 1.17 | −6.01 | −1.62 | 539.5 | −3.71 |
| I(d) | 1.05 | −5.89 | −1.74 | 571 | −3.72 |

A summary of the device layers and thicknesses is given in Table 3. In all cases the anode was ITO, as discussed above, the HT layer was MPMP, and the cathode was Al having a thickness in the range of 600-800 Å. In some cases, a second ET layer 150 was present. This layer comprised either tris(8-hydroxyquinolato)aluminum(III), Alq, or bis(2-methyl-8-quinolinolato)(para-phenyl-phenolato)aluminum(III), BAlq, as indicated.

Comparative examples, a-d, where no ET/AQ layer were used in the devices were also prepared. These comparative examples demonstrate it is necessary to use ET/AQ layer to achieve good device performance.

Comparative example a2 uses benzophenone as the ET/AQ layer, which yields very poor device performance. Benzophenone is white in color and has a band gap larger than that of EL compound I(a), which is yellow in color. This example demonstrates it is not sufficient to use a larger band gap material in the ET/AQ layer to block energy transfer.

Comparative examples a3 and a4 use compound I(c) as the ET/AQ layer, and either AlQ or BAlQ as the second electron transport layer. Relatively good device performance was obtained in spite of the fact that compound I(c) is orange in color which has a band gap smaller than that of compound I(a), which is yellow in color.

TABLE 3

| SAMPLE | HT, Å | EL, Å | ET/AQ, Å | ET, Å |
|---|---|---|---|---|
| Comparative a | 523 | I(a) 520 | | |
| 9-1 | 506 | I(a) 430 | II(b) 405 | |
| 9-2 | 507 | I(b) 407 | Comp. A 408 | |
| 9-3 | 507 | I(a) 405 | Comp. B 407 | |
| 9-4 | 505 | I(a) 404 | II(a) 305 | |
| 9-5 | 515 | I(a) 407 | II(c) 409 | |
| 9-6 | 508 | I(a) 411 | II(h) 416 | |
| 9-7 | 510 | I(a) 408 | II(i) 412 | |
| 9-8 | 516 | I(a) 419 | II(d) 406 | |
| 9-9 | 512 | I(a) 434 | II(g) 415 | |
| 9-10 | 505 | I(a) 415 | II(e) 432 | |
| 9-11 | 514 | I(a) 402 | II(f) 431 | |
| 9-12 | 545 | I(a) 403 | V(a) 430 | Alq 430 |
| 9-13 | 508 | I(a) 625 | V(b) 425 | |
| 9-14 | 509 | I(a) 413 | V(c) 416 | |
| 9-15 | 578 | I(a) 411 | V(d) 381 | |
| 9-16 | 549 | I(a) 425 | V(g) 423 | |
| 9-17 | 533 | I(a) 417 | VI(a) 411 | |
| 9-18 | 527 | I(a) 418 | V(e) 418 | |
| 9-19 | 502 | I(a) 403 | V(f) 106 | Alq 303 |
| 9-20 | 505 | I(a) 412 | V(k) 439 | |
| 9-21 | 514 | I(a) 416 | V(i) 408 | |
| 9-22 | 513 | I(a) 409 | V(h) 414 | |
| 9-23 | 515 | I(a) 500 | V(r) 410 | |
| 9-24 | 516 | I(a) 409 | V(l) 432 | |
| 9-25 | 504 | I(a) 412 | V(j) 402 | |
| Comparative a2 | 507 | I(a) 409 | Benzophenone 408 | |
| Comparative a3 | 519 | I(a) 411 | I(c) 110 | Alq 309 |
| Comparative a4 | 507 | I(a) 413 | I(c) 105 | BAlq 308 |
| Comparative b | 531 | I(b) 500 | | |
| 9-26 | 512 | I(b) 410 | Comp. A 406 | |
| 9-27 | 523 | I(b) 402 | Comp. B 416 | |
| Comparative c | 510 | I(c) 532 | | |
| 9-28 | 512 | I(c) 415 | II(g) 414 | |
| 9-29 | 516 | I(c) 401 | II(b) 408 | |
| 9-30 | 512 | I(c) 413 | Comp. B 407 | |
| 9-31 | 545 | I(c) 462 | Comp. A 111 | Alq 319 |
| 9-32 | 506 | I(c) 403 | II(d) 472 | |
| 9-33 | 503 | I(c) 404 | Comp. A 406 | |
| Comparative d | 511 | I(d) 508 | | |
| 9-34 | 504 | I(d) 411 | Comp. B 418 | |
| 9-35 | 511 | I(d) 418 | II(d) 407 | |
| 9-36 | 512 | I(d) 404 | II(g) 402 | |
| 9-37 | 509 | I(d) 409 | II(b) 409 | |
| 9-38 | 516 | I(d) 411 | II(a) 406 | |

The devices were tested as described above and the results are given in Table 4 below.

TABLE 4

| SAMPLE | PEAK RADIANCE cd/m$^2$ | PEAK EFFICIENCY cd/A | APPROXIMATE PEAK WAVELENGTHS nm |
|---|---|---|---|
| Comparative a | 4 at 21 V | 0.01 | 525 |
| 9-1 | 3500 at 19 V | 17 | 525 |
| 9-2 | 3000 at 22 V | 10 | 525 |
| 9-3 | 4500 at 19 V | 20 | 525 |

TABLE 4-continued

| SAMPLE | PEAK RADIANCE cd/m² | PEAK EFFICIENCY cd/A | APPROXIMATE PEAK WAVELENGTHS nm |
|---|---|---|---|
| 9-4 | 3500 at 20 V | 11 | 525 |
| 9-5 | 1200 at 25 V | 6 | 525 |
| 9-6 | 1900 at 24 V | 8 | 525 |
| 9-7 | 1600 at 28 V | 8.5 | 525 |
| 9-8 | 2200 at 25 V | 16 | 525 |
| 9-9 | 400 at 21 V | 11 | 525 |
| 9-10 | 1000 at 23 V | 6 | 525 |
| 9-11 | 900 at 27 V | 8.5 | 525 |
| 9-12 | 2300 at 20 V | 5.4 | 525 |
| 9-13 | 2700 at 27 V | 10 | 525 |
| 9-14 | 400 at 15 V | 10 | 525 |
| 9-15 | 90 at 22 V | 4.4 | 525 |
| 9-16 | 2000 at 23 V | 13 | 525 |
| 9-17 | 80 at 20 V | 0.01 | 525 |
| 9-18 | 200 at 22 V | 1.1 | 525 |
| 9-19 | 7000 at 15 V | 30 | 525 |
| 9-20 | 1600 at 22 V | 11 | 525 |
| 9-21 | 300 at 19 V | 2.6 | 525 |
| 9-22 | 1200 at 20 V | 9.5 | 525 |
| 9-23 | 220 at 26 V | 2.6 | 525 |
| 9-24 | 100 at 22 V | 1.2 | 525 |
| 9-25 | 180 at 25 V | 8.5 | 525 |
| Comparative a2 | 16 at 21 V | 0.2 | 525 |
| Comparative a3 | 3000 at 22 V | 7 | 525 |
| Comparative a4 | 750 at 22 V | 7 | 525 |
| Comparative b | 160 at 20 V | 0.1 | 522 |
| 9-26 | 700 at 24 V | 4 | 522 |
| 9-27 | 130 at 24 V | 1.8 | 522 |
| Comparative c | 30 at 15 V | 0.1 | 560 |
| 9-28 | 2400 at 23 V | 13 | 560 |
| 9-29 | 1400 at 20 V | 6.5 | 560 |
| 9-30 | 2200 at 18 V | 5.8 | 560 |
| 9-31 | 510 at 20 V | 2.2 | 560 |
| 9-32 | 1700 at 22 V | 10 | 560 |
| 9-33 | 2000 at 27 V | 5 | 560 |
| Comparative d | 0.1 at 20 V | 0.015 | |
| 9-34 | 190 at 26 V | 1.5 | 570 |
| 9-35 | 30 at 26 V | 1.1 | 570 |
| 9-36 | 200 at 24 V | 2 | 570 |
| 9-37 | 50 at 25 V | 0.8 | 570 |
| 9-38 | 430 at 25 V | 2.5 | 570 |

The peak efficiency is the best indication of the value of the electroluminescent compound in a device. It gives a measure of how many electrons have to be input into a device in order to get a certain number of photons out (radiance). It is a fundamentally important number, which reflects the intrinsic efficiency of the light-emitting material. It is also important for practical applications, since higher efficiency means that fewer electrons are needed in order to achieve the same radiance, which in turn means lower power consumption. Higher efficiency devices also tend to have longer lifetimes, since a higher proportion of injected electrons are converted to photons, instead of generating heat or causing an undesirable chemical side reactions.

As can be seen in the comparative examples of Table 4, devices made without the ET/AQ layer have much lower electroluminescence efficiency than devices made with the ET/AQ layer. Also, for a given photoactive material, different device efficiency can be obtained with different ET/AQ materials, although all of these ET/AQ materials have band gap larger than the energy of the luminescent exciton. This shows that to prevent the quenching of the luminescent exciton, it is not sufficient just to block the energy transfer process. The electron transfer process also has to be blocked. This is done via method outlined in criteria 1-4. Therefore to obtain a maximal electroluminescence efficiency, there exists at least one optimal, matched ET/AQ material for each different electroluminescent material as shown in Table 4.

Figure 15:
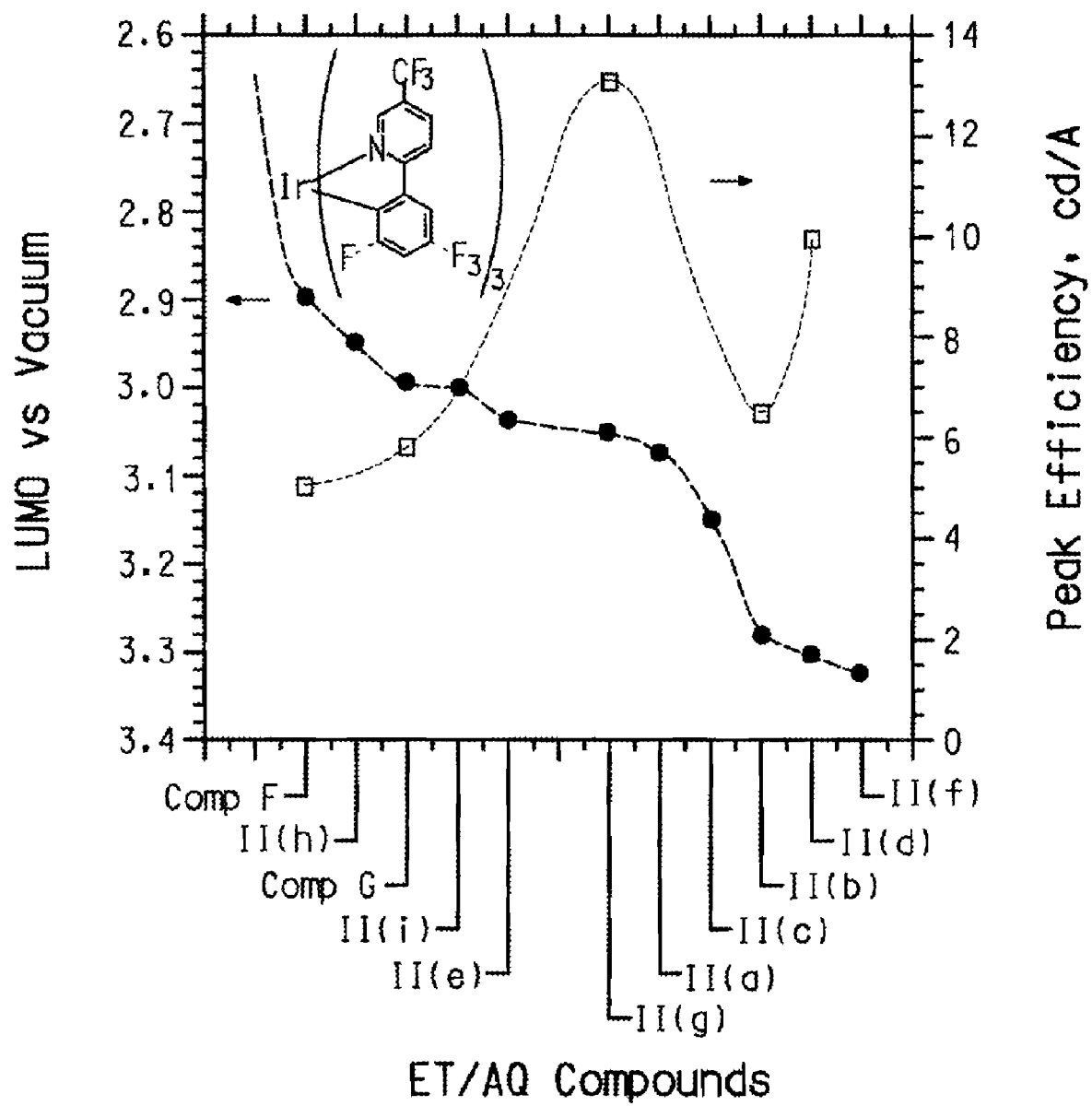
FIG. 15 is a diagram of EL efficiency for devices using iridium complex I(a).
Figure 16:
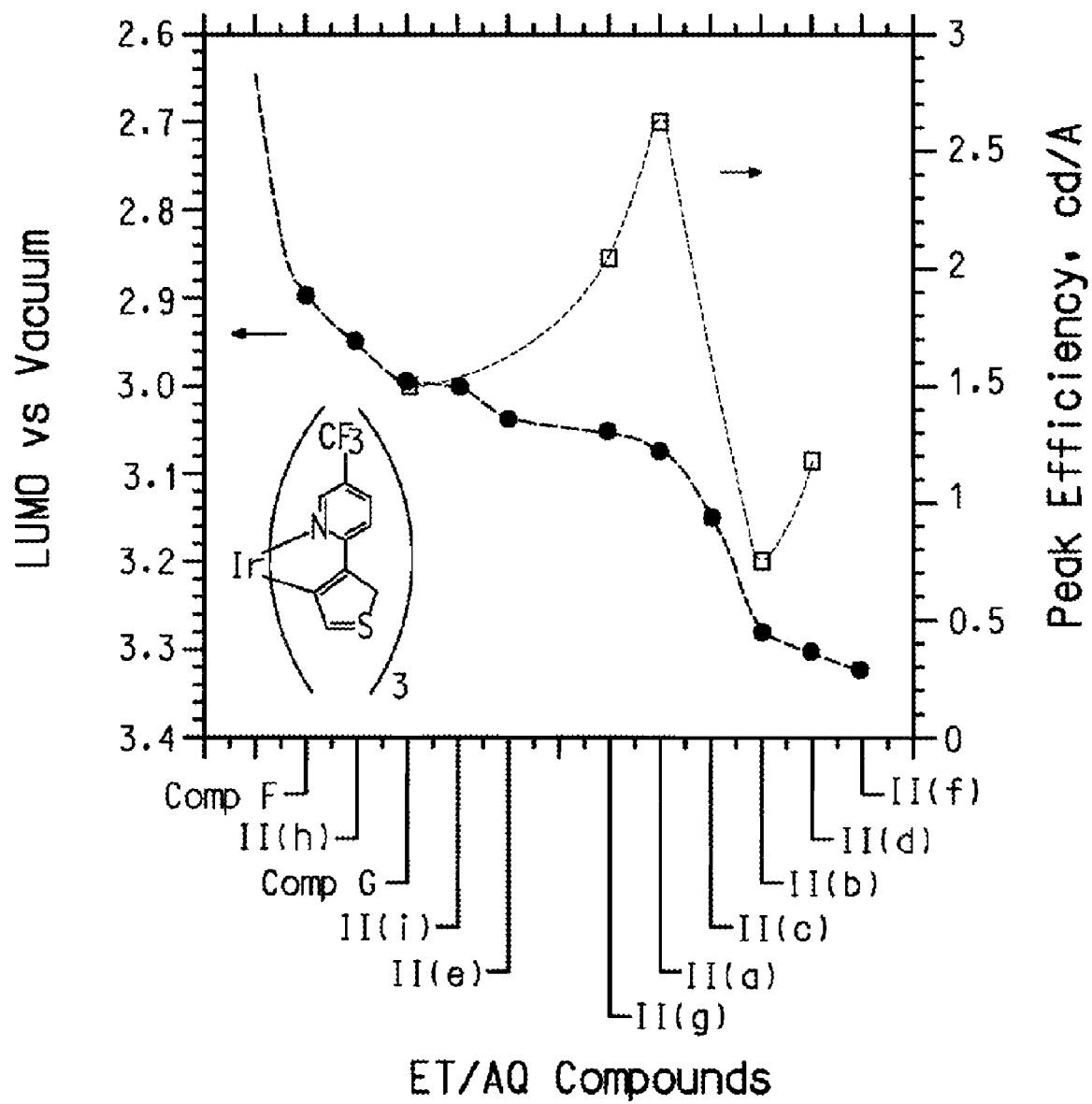
FIG. 16 is a diagram of EL efficiency for devices using iridium complex I(b).
Figure 17:
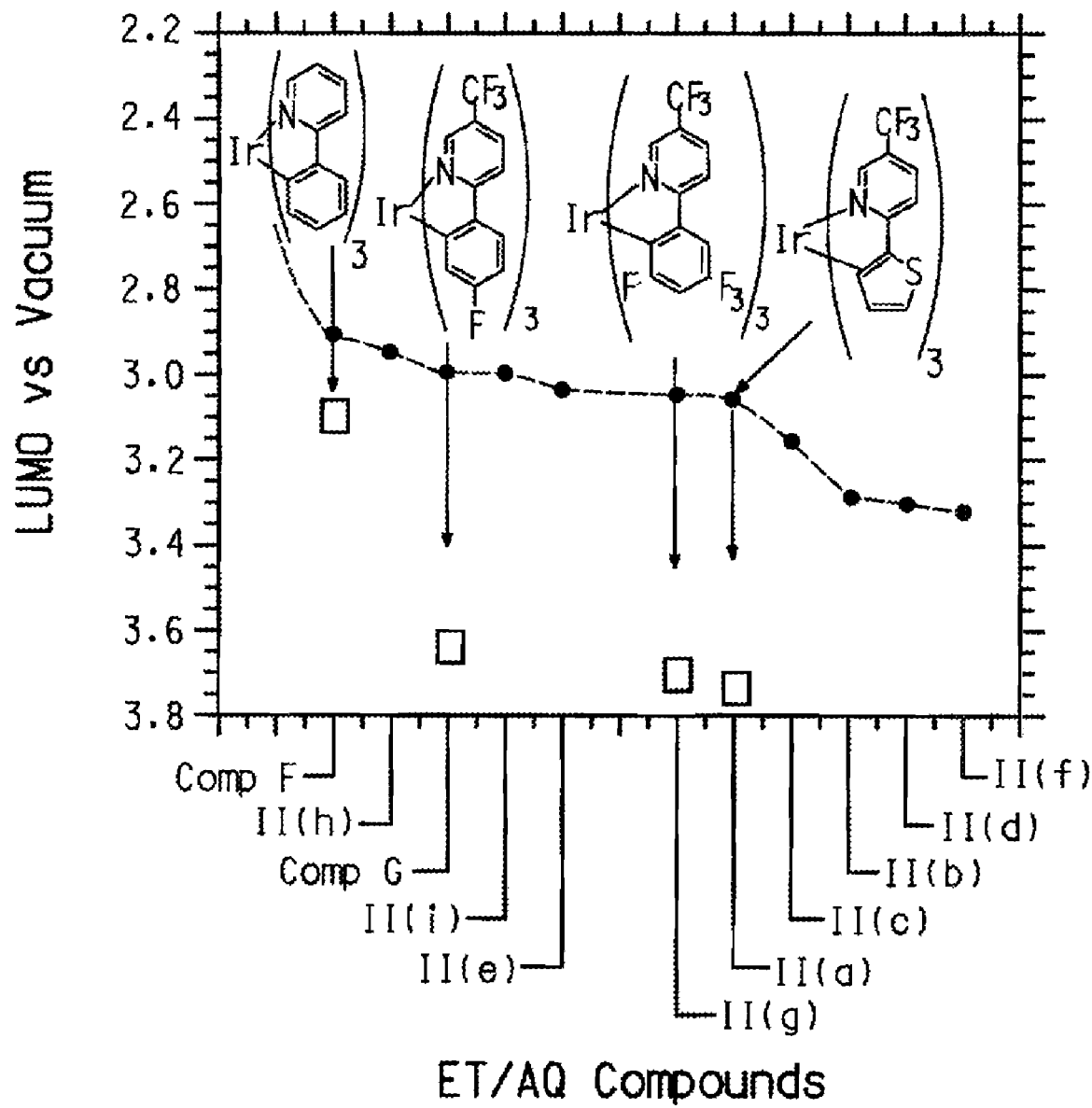
FIG. 17 is a plot showing the best ET/AQ compositions for different iridium complex emitters.
Figure 18:
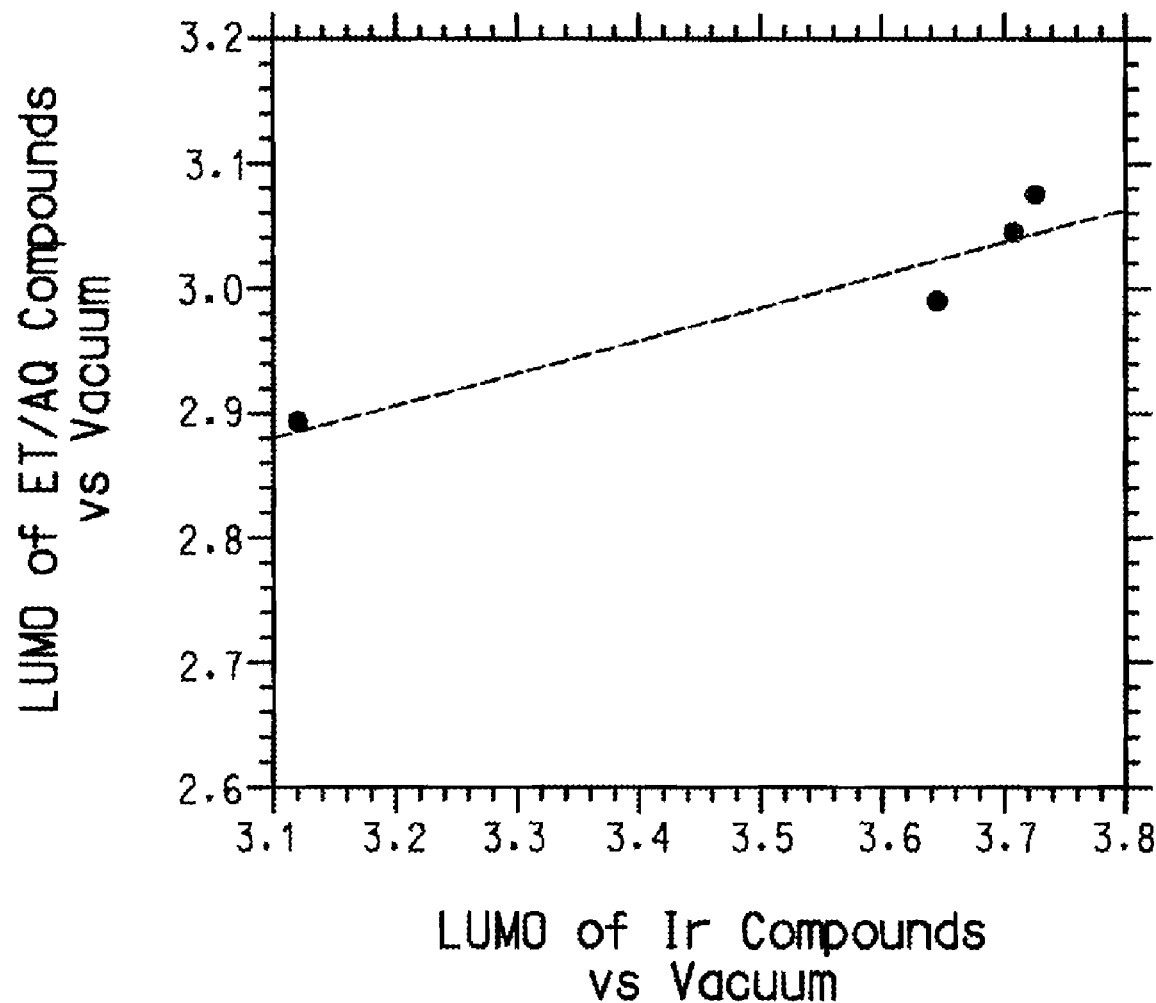
FIG. 18 is a plot of the LUMO of the iridium complex emitters vs the LUMO of ET/AQ compositions.

As examples, the dependence of electroluminescence efficiency on the LUMO energies of the ET/AQ compounds are plotted in FIG. 15 and FIG. 16 for emitters I(c) and I(d), respectively. For each photoactive material, the efficiency is quite sensitive to the ET/AQ compound used and an optimal ET/AQ compound can be found by tuning the ET/AQ LUMO energy. FIG. 17 plots the best ET/AQ compound for all the emitters studied here. As can be seen there is a general correlation between the LUMO of the ET/AQ compound and the LUMO of the emitter, within experimental uncertainty. As the emitter LUMO energy decreases, there is a corresponding decrease in the LUMO energy of the best ET/AQ material. FIG. 18 plots the LUMO of the best ET/AQ compound (y) vs. the LUMO of the corresponding emitter (x). The data can be roughly fitted with a linear equation of $y=2(\pm 0.1)+0.273 \cdot x$

The invention claimed is:

1. A photoactive electronic device comprising:
    (a) an anode;
    (b) a cathode, said cathode having a work function energy level $E3$;
    (c) a photoactive layer positioned between said anode and said cathode, said photoactive layer comprising a cyclometalated complex of a transition metal, said cyclometalated complex having a LUMO energy level $E2$ and a HOMO energy level $E4$; and
    (d) an electron transport and/or anti-quenching layer, at least one of the electron transport or anti-quenching layer comprising a quinoxaline derivative, positioned between said cathode and said photoactive layer, said electron transport and/or anti-quenching layer having a LUMO energy level E1 and a HOMO energy level E5, with the proviso that:
(1) E1−E3<1 eV,
(2) E1−E2>−1 eV, and
(3) E4−E5>−1 eV and; wherein the quinoxaline derivative is selected from Formulae VI(a), and VI(h):

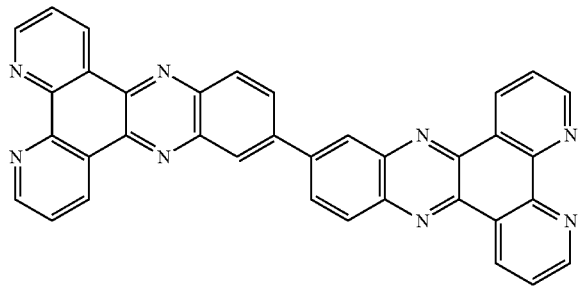

VI(a)

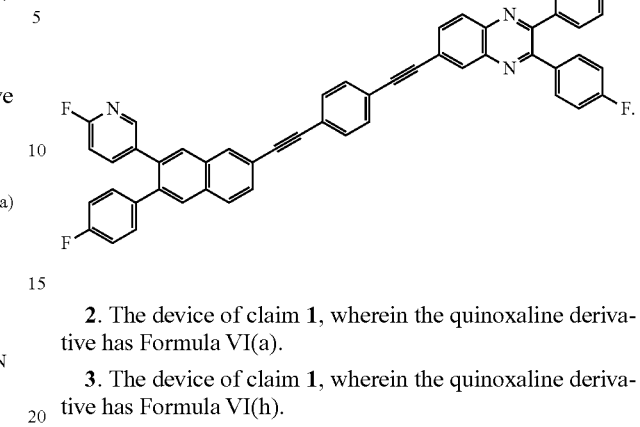

VI(h)

2. The device of claim 1, wherein the quinoxaline derivative has Formula VI(a).

3. The device of claim 1, wherein the quinoxaline derivative has Formula VI(h).

* * * * *